US007888120B2

(12) United States Patent
Klein et al.

(10) Patent No.: US 7,888,120 B2
(45) Date of Patent: Feb. 15, 2011

(54) GLOBAL REGULATOR OF MORPHOGENESIS AND PATHOGENICITY IN DIMORPHIC FUNGI AND USES THEREOF

(75) Inventors: Bruce S. Klein, Madison, WI (US); Julie C. Nemecek, Madison, WI (US); Marcel Wuethrich, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 368 days.

(21) Appl. No.: 11/734,576

(22) Filed: Apr. 12, 2007

(65) Prior Publication Data

US 2008/0038201 A1 Feb. 14, 2008

Related U.S. Application Data

(60) Provisional application No. 60/791,811, filed on Apr. 13, 2006.

(51) Int. Cl.
*C12N 15/00* (2006.01)

(52) U.S. Cl. ...................................... 435/440; 435/455

(58) Field of Classification Search ................ 536/23.1, 536/24.3, 24.33, 24.5
See application file for complete search history.

(56) References Cited

PUBLICATIONS

Ochiai et al. (Biosci. Biotechnol. Bichem, 2002 vol. 66(10):2209-2215).*
Calera et al. (Infection and Immunity, 1999 vol. 67(8):4280-4284).*
Nagahashi et al. (Microbiology, 1998 vol. 144:425-432).*
Pott et al. (Fungal Genetics and Biology, 2000 vol. 31:55-67).*
Ajello et al., Histoplasmosis 103-22 (1971).
Alex et al., Proc Natl Acad Sci U S A 95, 7069 (1998).
Beijersbergen et al., Science 256, 1324 (1992).
Boone et al., J Cell Biol 110, 1833 (1990).
Brandhorst et al., J Exp Med 189, 1207 (1999).
Chiller et al., Infect Dis Clin North Am 17, 41 (Mar. 2003).
Davis et al., Methods Enzymol 17A, 79 (1970).
Deschenes et al., Antimicrob Agents Chemother 43, 1703 (1999).
Dijkgraaf et al., Yeast 12, 683 (1996).
Fisher et al., Biostatistics: Methodology for the Health Sciences 611-613 (1993).
Galgiani, Ann Intern Med 130, 293 (1999).
Hogan et al., Infect Immun 62, 3543 (1994).
Klein et al., J Clin Invest 85, 152 (1990).
Klein et al., Semin Respir Infect 1, 29 (1986).
Klimpel et al., Infect Immun 56, 2997 (1988).
Koresawa et al., Assay Drug Dev Technol 2, 153 (2004).
Krems et al., Curr Genet 29, 327 (1996).
Lehmann et al., Infect Immun 12, 987 (1975).
Li et al., Embo J 17, 6952 (1998).
Maeda et al., Mol Cell Biol 13, 5408 (1993).
Maresca et al., Microbiol Rev 53, 186 (1989).

(Continued)

*Primary Examiner*—Sean McGarry
*Assistant Examiner*—Terra Cotta Gibbs
(74) *Attorney, Agent, or Firm*—Quarles & Brady, LLP

(57) ABSTRACT

A method of screening a compound for anti-fungal properties comprising the steps of exposing a test compound to a fungal histidine kinase, and determining whether kinase activity is inhibited, wherein inhibition of kinase activity indicates that the compound has anti-fungal properties is disclosed.

3 Claims, 12 Drawing Sheets

OTHER PUBLICATIONS

Medoff et al., Science 231, 476 (1986).
Nemecek et al., Science 312, 583 (2006).
Nosanchuk et al., Cell Microbiol 5, 203 (2003).
Ota et al., Science 262, 566 (1993).
Posas et al., Cell 86, 865 (1996).
Rappleye et al., Mol Microbiol 53, 153 (2004).
Rinaldi et al., J Clin Microbiol 15, 1159 (1982).
Rooney et al., Mol Microbiol 39, 875 (2001).
Salazar et al., Infect Immun 56, 711 (1988).
Santos et al., Sci STKE 2001, RE1 (2001).
Sebghati et al., Science 290, 1368 (2000).
Shieh et al., Mol Biol Cell 9, 311 (1998).
Stock, Curr Biol 9, R364 (1999).
Sullivan et al., Eukaryot Cell 1, 895 (2002).
Van der Vaart, et. al., J Bacteriol 177, 3104 (1995).
Wheat et al., Medicine (Baltimore) 69, 361 (1990).
White et al., Cell Mol Life Sci 53, 744 (1997).
Winkler et al., Eukaryot Cell 1, 163 (2002).
Worsham et al., J Med Vet Mycol 26, 137 (1988).
Wüthrich et al., J. Clin Invest 106:1381-1389 (2000).
Wuthrich et al., J Exp Med 197, 1405 (2003).
Yamada-Okabe et al., J Bacteriol 181, 7243 (1999).
http://genome.wustl.edu/blast/blasto_client.cgi.

* cited by examiner

A

B

A

B

GLOBAL REGULATOR OF MORPHOGENESIS AND PATHOGENICITY IN DIMORPHIC FUNGI AND USES THEREOF

CROSS-REFERENCE TO RELATED APPLICATIONS

This application claims the benefit of U.S. Provisional Patent Application No. 60/791,811, filed Apr. 13, 2006, which is incorporated herein by reference as if set forth in its entirety.

STATEMENT REGARDING FEDERALLY SPONSORED RESEARCH OR DEVELOPMENT

This invention was made with United States government support awarded by the following agency: NIH Grants AI035681 and AI050882. The United States has certain rights in this invention.

BACKGROUND OF THE INVENTION

Microbial pathogens that inhabit our environment must undergo a radical change to survive inside a mammalian host. Among the more than 100,000 different species of environmental fungi are six phylogenetically related ascomycetes called the dimorphic fungi: *Blastomyces dermatitidis, Coccidioides immitis, Histoplasma capsulatum, Paracoccidioides brasiliensis, Sporothrix schenkii*, and *Penicillium marneffei*. These fungi change morphology once spores are inhaled into the lungs of a mammalian host from hyphal molds in the environment to pathogenic yeast forms. Dimorphic fungi inhabit the soil worldwide and collectively cause over a million new infections a year in the United States alone. They tend to remain latent after infection and may reactivate if the subject becomes immune-deficient (J. N. Galgiani, *Ann Intern Med* 130, 293 (1999); L. Ajello, *Distribution of Histoplasma capsulatum in the United States*. C. W. Ajello L, Furcolow M F, Ed., *Histoplasmosis* (Charles C. Thomas Publishers, Springfield Ill., 1971), pp. 103-22; L. J. Wheat et al., *Medicine* (Baltimore) 69, 361 (1990); T. M. Chiller, J. N. Galgiani, D. A. Stevens, *Infect Dis Clin North Am* 17, 41 (Mar, 2003); B. S. Klein, J. M. Vergeront, J. P. Davis, *Semin Respir Infect* 1, 29 (1986).). It has long been believed that phase transition from mold to yeast is obligatory for pathogenicity, but the mechanism that regulates this switch has remained a mystery. In this report, we provide firm genetic evidence that establishes the central role of dimorphism in pathogenicity, and describe a regulator of this morphologic transition.

It is temperature that induces dimorphic fungi to change phases (B. Maresca, G. S. Kobayashi, *Microbiol Rev* 53, 186 (1989).). At 25° C., they grow as mold. At 37° C., the core temperature of humans, they switch into the pathogenic yeast form (G. Medoff et al., *Science* 231, 476 (1986).), during which yeast-phase specific virulence genes are induced. Few of these genes have been identified; among the best studied are BAD1 of *B. dermatitidis*, CBP1 of *H. capsulatum* and the α-(1,3)-glucan synthase (AGS1) of these fungi and *P. brasiliensis* (B. S. Klein, J. M. Jones, *J Clin Invest* 85, 152 (1990); T. S. Sebghati, J. T. Engle, W. E. Goldman, *Science* 290, 1368 (2000); L. H. Hogan, B. S. Klein, *Infect Immun* 62, 3543 (1994).). We postulated that deciphering the regulation of phase-specific genes would elucidate the control of morphogenesis.

Forward genetics, a process of inducing mutations randomly in a genome to detect phenotypes and linked genes, has advanced our understanding of microbial pathogenesis. Dimorphic fungi have not yet been manipulated in this way because the classical genetic approaches have proved too cumbersome and the molecular tools have been unavailable. We previously showed that *Agrobacterium tumefaciens* transfers DNA randomly into the genomes of *B. dermatitidis* and *H. capsulatum*, primarily into single sites and without recombination, in theory, allowing the identification of recessive mutations (T. D. Sullivan, P. J. Rooney, B. S. Klein, *Eukaryot Cell* 1, 895 (2002).). In the present invention, we disclose the use of *A. tumefaciens* for insertional mutagenesis in a dimorphic fungus to attempt to uncover regulators of yeast-phase specific genes and phase transition from mold to yeast.

SUMMARY OF THE INVENTION

In one embodiment, the present invention is a method of screening a compound for anti-fungal properties comprising the steps of (a) exposing a test compound to a fungal histidine kinase, preferably DRK1, and (b) determining whether kinase activity is inhibited, wherein inhibition of kinase activity indicates that the compound has anti-fungal properties. In one specific embodiment, the exposure of the test compound to a fungal histidine kinase is in vitro. In another embodiment, the exposure is in vivo.

In one embodiment, the determination of (b) is via examination of a luminescent signal and/or the exposure of step (a) is to at least 90 samples simultaneously.

In another embodiment, the invention is a dimorphic fungi, wherein the fungi has a reduced histidine kinase expression and wherein the fungi has a reduced ability to morph into the virulent yeast form.

In another embodiment, the invention is a method of vaccinating a patient, comprising the step of treating the patient with a vaccine comprising a fungi with reduced histidine kinase expression and wherein the fungi has a reduced ability to morph into the virulent yeast form. Preferably the vaccine is an attenuated vaccine for *B. dermatitidis* or *H. capsulatum*.

Sporulation of mold. Left: sporulating hyphae of the wild-type and mutant strain on potato flake agar. Right: total number of spores produced after two weeks of growth at 22° C. Data are representative of two experiments. Scale bar, 10 microns.

Figure 2:
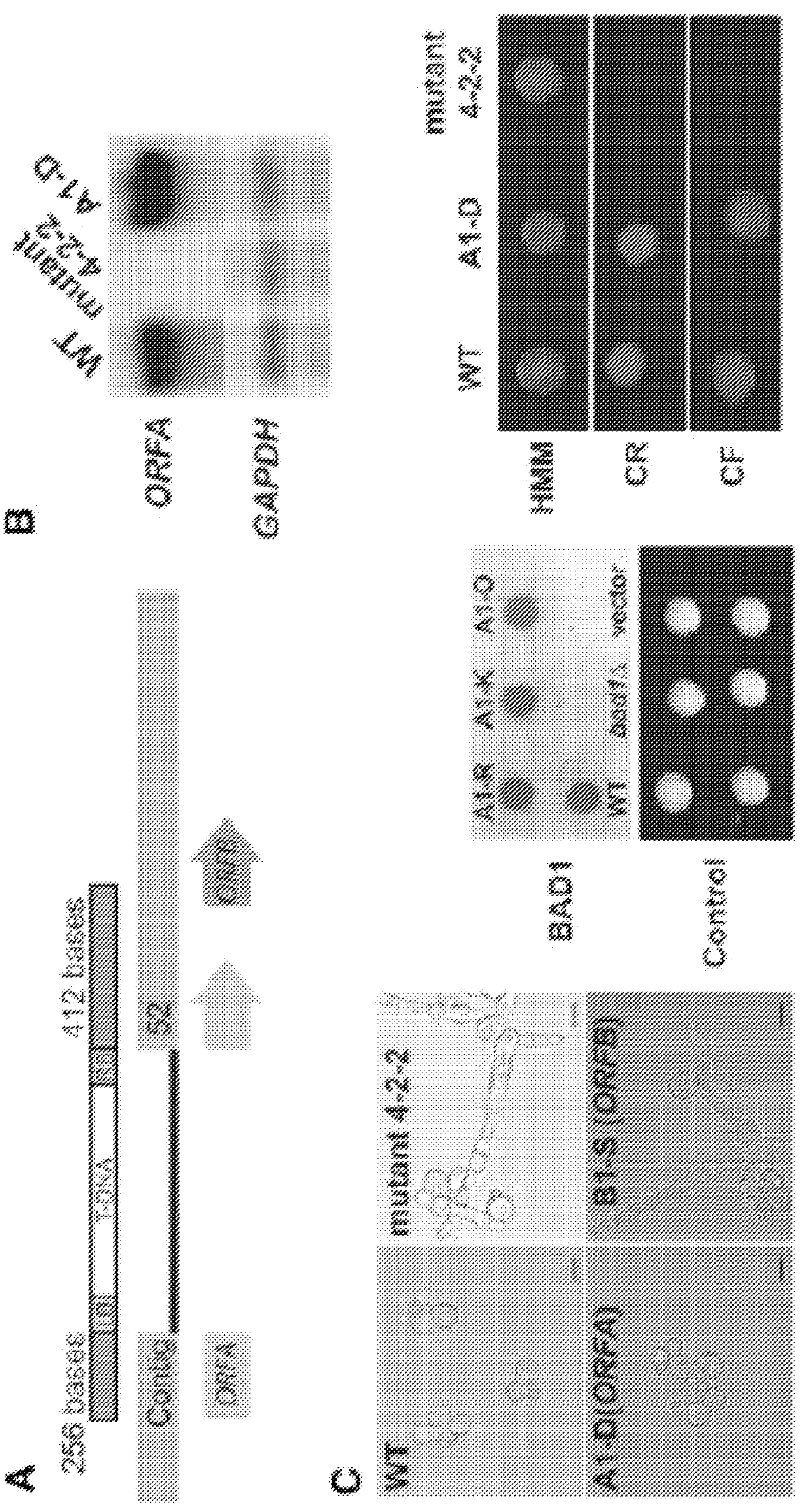
Figure 2:
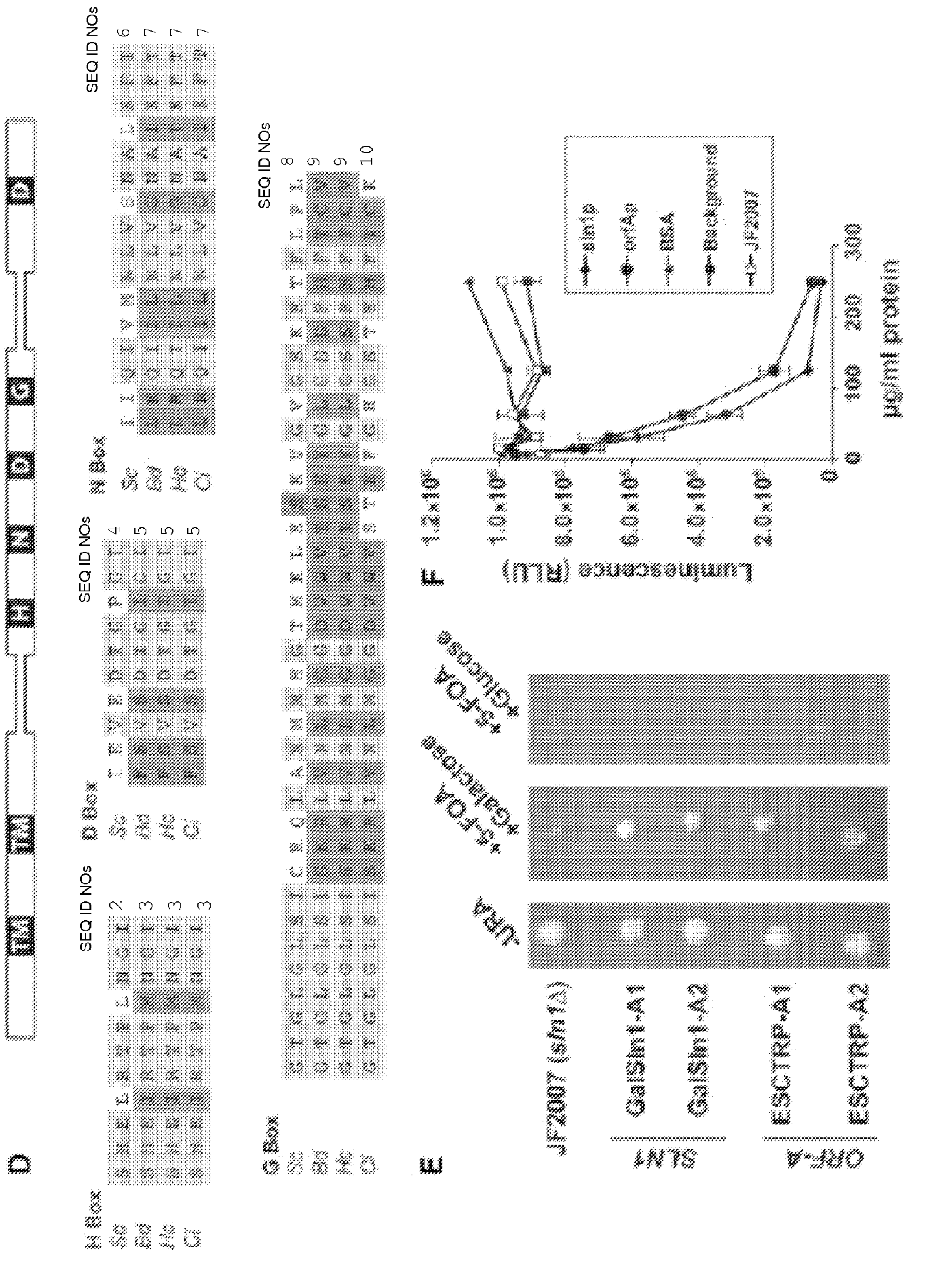

FIG. 2. Elucidation of the genotype of mutant 4-2-2. (A) A single T-DNA insertion is present in the mutant. 256 bases on the left border and 412 bases on the right were identified by adapter PCR. Flanks have homology to contig 52 in the *Blastomyces* genome. Putative ORFs (A and B) are located near the insertion. T-DNA inserted into the 3825 nucleotide ORFA coding sequence 522 nucleotides upstream of the stop codon. The insertion interrupts the first β-sheet of the protein's receiver domain (see FIG. 2D). ORFB is 1.4 kb away from the T-DNA insertion. "LB" denotes the T-DNA left border, and "RB" the right border. (B) Northern analysis of ORFA transcript. A1-D is a transformant of mutant 4-2-2 complemented with an intact genomic copy of ORFA and flanking sequence. (C)ORFA complements the defects in 4-2-2. Left: ORFA restores yeast morphology to mutant 4-2-2, whereas ORFB does not. Middle: fungal colony immunoblot for BAD1. In transformants re-expressing ORFA (A1-R, A1-K, A 1-O), BAD-1 is detectable. bad1Δ strain 55, and a transformant of strain 4-2-2 that received a control vector lacking ORFA ("vector"), are negative controls. The patches of fungal cells tested are shown below the blot. Right: growth of mutant, WT, and a complemented strain A1-D on HMM in the presence of calcofluor (CF) or Congo red (CR) (20 μg/mL). Growth of the strains on HMM alone is shown above. Scale bar, 10 microns. (D) ORFA has the domain structure and sequence of histidine kinase and is conserved in dimorphic fungi. ORFA has a histidine-containing H box, an aspartate containing D-box and G and N boxes (J. Stock, *Curr Biol* 9, R364 (1999).). Two putative transmembrane domains (TM) and an aspartate containing receiver domain at the C-terminus are also present. Sequences homologous to the *S. cerevisiae* (Sc) histidine kinase SLN1 and *B. dermatitidis* (Bd) histidine kinase are present in other dimorphic fungi *H. capsulatum* (Hc) and *C. immitis* (Ci). (E) *Blastomyces* ORFA complements an sln1 defect in *S. cerevisiae*. *S. cerevisiae* JF2007 (slnl:LEU2, ura3-52, trp1Δ63, his3Δ200, leu2Δ1, lys2, pRSPTP2 [URA3]) was transformed with a galactose-inducible vector containing a c-myc tagged SLN1 (pGalSln1-A1 and A2) or a F1AG-tagged ORFA (pESCTRP-422-A1 and A2). Both vectors contained TRP1 for selection. Transformants were initially plated on medium lacking uracil to select for pRSPTP2, and lacking tryptophan to select for the expression vector. Transformants were then plated on medium containing 5-FOA to select against pRSPTP2, and containing galactose for induction. pRSPTP2 rescues the lethal sln1 defect. Only transformants with a functional histidine kinase that complements the snl1 defect can grow on 5-FOA media under inducing conditions (I. M. Ota, A. Varshavsky, *Science* 262, 566 (1993).). Transformants were plated on 5-FOA containing medium with glucose as a control for gene induction. (F) Kinase activity detected by a luminescent assay. Decreasing relative light units (RLU) indicates increasing kinase activity. Protein was immunoprecipitated from *S. cerevisiae* JF2007 transformed with c-myc tagged SLN1 expression vector (Sln1p), FLAG-tagged ORFA expression vector (orfAp), or untransformed JF2007 (JF2007), using anti-myc or anti-flag antibody. BSA and reaction buffer (background) are negative controls. Data are the mean ±SD of three experiments.

Figure 3:
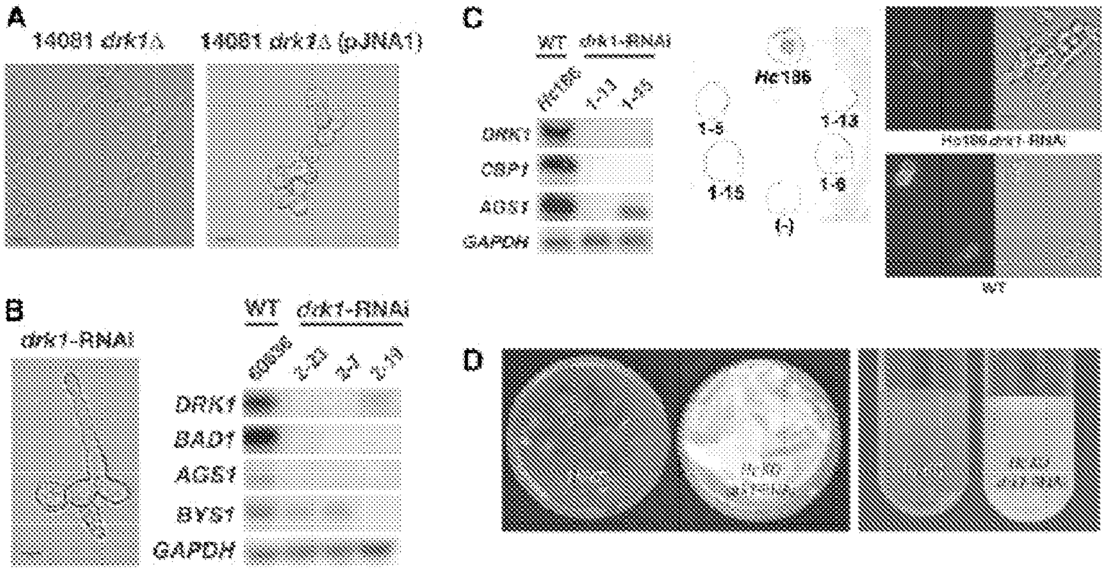

FIG. 3. The histidine kinase DRK1 regulates dimorphism from mold to yeast and virulence gene expression in *B. dermatitidis* and *H. capsulatum*. (A) Left: knockout strain (14081 DRK1Δ) grown at 37° C. is locked in the mold morphology. Right: complemented strain 14081 DRK1Δ (pJNA1) regains the parental yeast phenotype at 37° C. Scale bar, 10 microns. (B) Left: Gene silencing of DRK1 by RNAi in *B. dermatitidis* 60636 (DRK1-RNAi) induces pseudohyphal morphology at 37° C. Scale bar, 10 microns. Right: Northern analysis of virulence factors BAD1 and AGS1 and yeast-phase specific gene BYS1 in three independent DRK1-silenced transformants of *B. dermatitidis* parental strain 60636. GAPDH, loading control. (C) Left panel: Northern analysis of two independent DRK1-silenced transformants of *H. capsulatum* strain 186AR ura5, probing for the expression of DRK1 and virulence genes CBP1 and AGS1. Middle panel: ruthenium red stain of CBP1 in culture supernatant. Four independent DRK1-silenced transformants of *H. capsulatum* (1-5, 1-13, 1-15, and 1-6) show decreased staining compatible with reduced CBP1. Parental strain 186AR ura5 is a positive control, and medium (−) a negative control. Right panel: surface α-(1,3)-glucan in a DRK1-silenced strain of *H. capsulatum* (Hc186 DRK1-RNAi) and parental 186AR ura5 (WT). Cells were stained with mAb MOPC104e and goat anti-mouse fluorescein isothiocyanate (Materials and methods are available as supporting material on Science online.). Light image is on the right. Scale bar, 10 microns. (D) Pigmentation of *H. capsulatum* wild-type (HcKD) and DRK1-silenced strain (HcKD drk1-RNAi). Mold on agar plates (left) and a suspension of the harvested spores (right).

Figure 4:
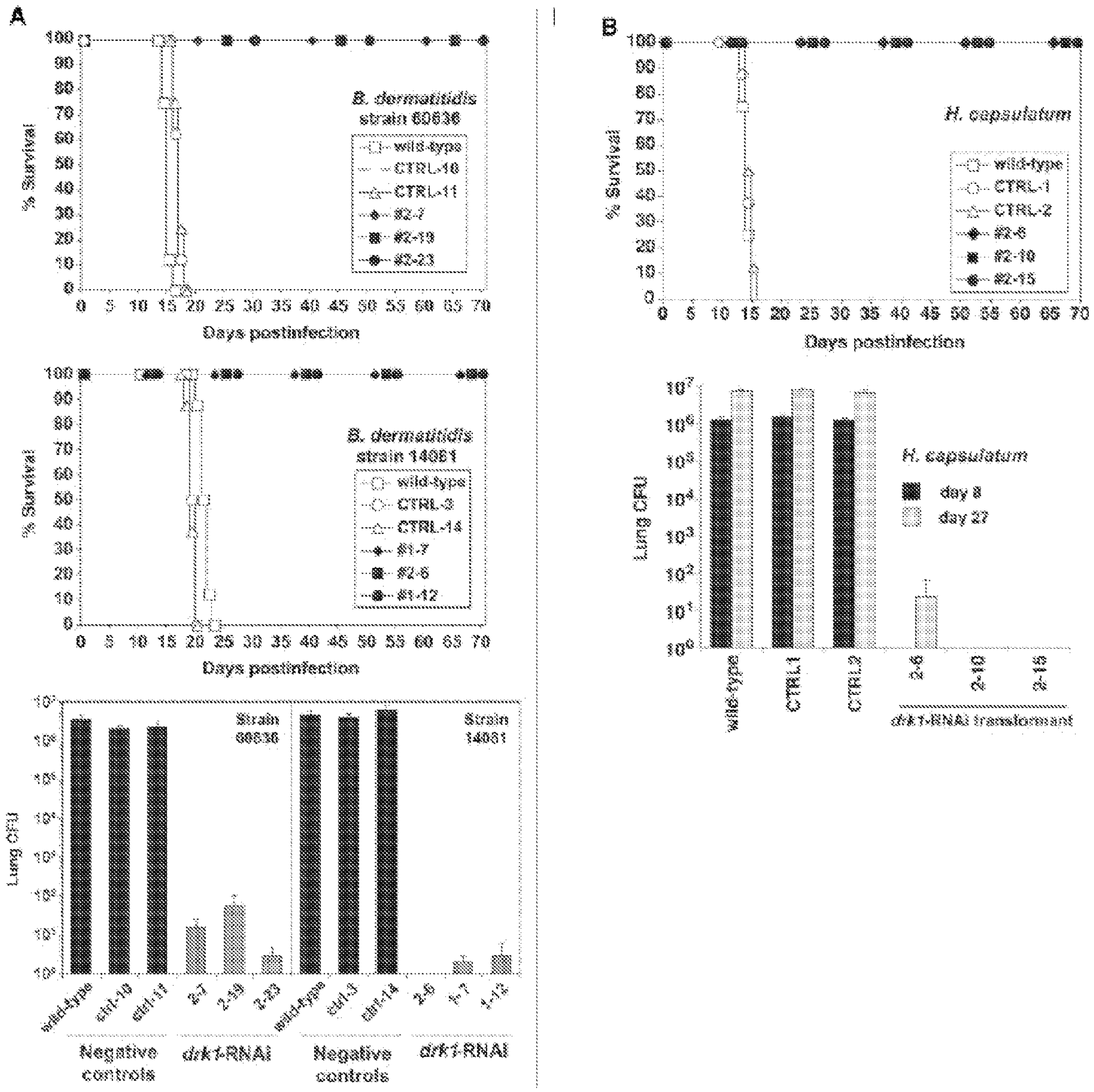
Figure 10:
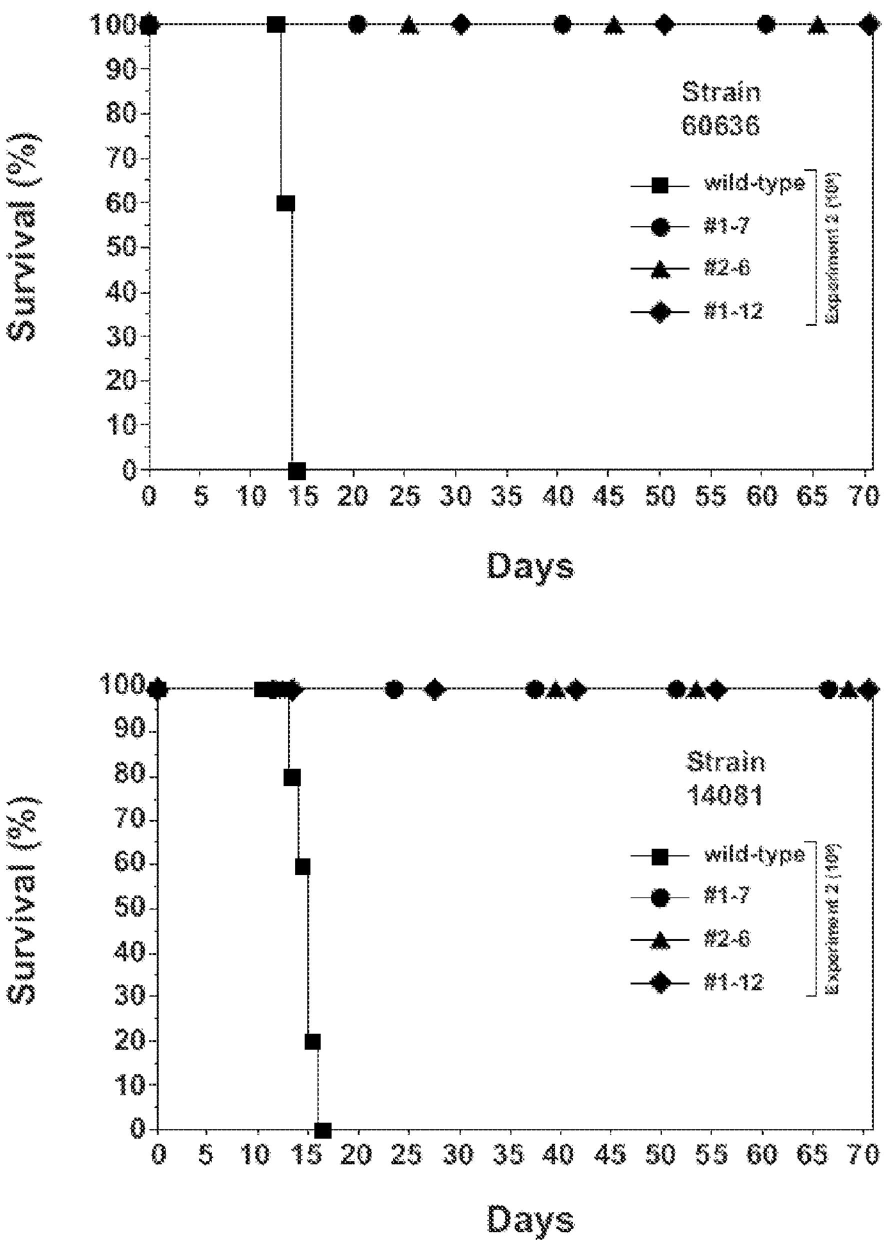

FIG. 4. Effect of knocking down DRK1 expression on the in vivo pathogenicity of *B. dermatitidis* and *H. capsulatum* in murine models of pulmonary infection. (A) Spores of DRK1-silenced transformants from *Blastomyces* strains 60636 and 14081 were used to infect C57BL6 mice. Mice (n=10/group) received $10^4$ spores intratracheally. The wild-type strain, three independent DRK1-silenced transformants, and two control (CTRL) transformants that received an RNAi vector lacking the target sequence were studied. Upper panels: survival. Middle panel: burden of lung infection (CFU) in mice 14 days after infection. $p<0.001$, for survival and lung CFU in the gene-silenced transformants vs. wild-type and control strains. Results were similar when mice were infected with 100-fold more spores ($10^6$) of DRK1-silenced transformants (FIG. 10). (B) Spores of DRK1-silenced transformants of *Histoplasma* clinical isolate "KD" were used to infect C57BL6 mice. Mice (n=10/group) received $10^8$ spores intratracheally. The wild-type strain, three independent DRK1-silenced transformants, and two control (CTRL) transformants that received an RNAi vector lacking target sequence were studied. Lower left: survival. Lower right: lung infection (CFU) eight and 27 days after infection. $p<0.001$, for survival and lung CFU in gene-silenced transformants vs. wild-type and control strains.

FIG. 4. Effect of knocking down DRK1 expression on the in vivo pathogenicity of *B. dermatitidis* and *H. capsulatum* in murine models of pulmonary infection. (A) Spores of DRK1-silenced transformants from *Blastomyces* strains 60636 and 14081 were used to infect C57BL6 mice. Mice (n=10/group) received $10^4$ spores intratracheally. The wild-type strain, three independent DRK1-silenced transformants, and two control (CTRL) transformants that received an RNAi vector lacking the target sequence were studied. Upper panels: survival. Middle panel: burden of lung infection (CFU) in mice 14 days after infection. $p<0.001$, for survival and lung CFU in the gene-silenced transformants vs. wild-type and control strains. Results were similar when mice were infected with 100-fold more spores ($10^6$) of DRK1-silenced transformants (FIG. 10). (B) Spores of DRK1-silenced transformants of *Histoplasma* clinical isolate "KD" were used to infect C57BL6 mice. Mice (n=10/group) received $10^8$ spores intratracheally. The wild-type strain, three independent DRK1-silenced transformants, and two control (CTRL) transformants that received an RNAi vector lacking target sequence were studied. Lower left: survival. Lower right: lung infection (CFU) eight and 27 days after infection. p<0.001, for survival and lung CFU in gene-silenced transformants vs. wild-type and control strains.

Figure 5:
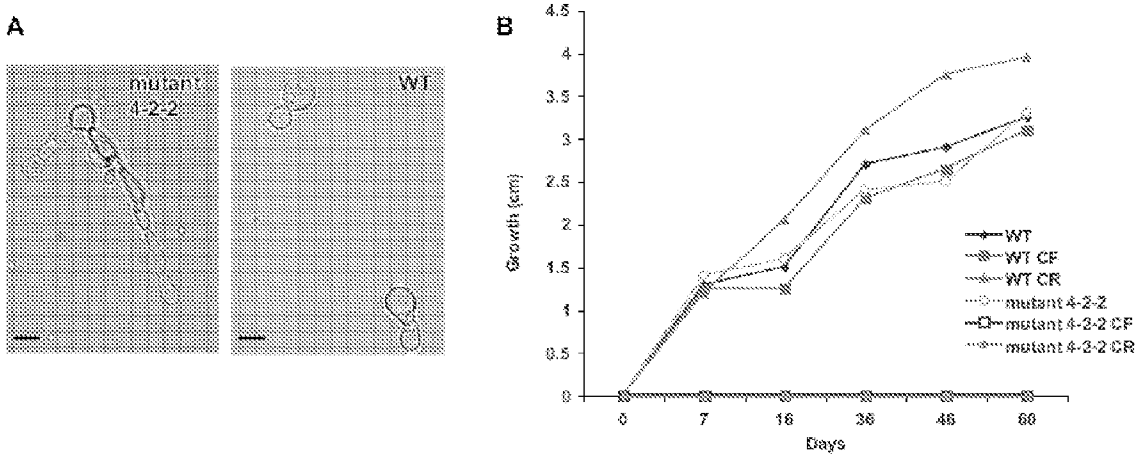

FIG. 5. Additional phenotypes of the mutant 4-2-2. (A) Germinated spores of the mutant 4-2-2 and wild-type (WT) parental strain T53-19. Spores were generated and harvested as described in the supplementary methods. Spores were plated on 3M medium and grown at 37° C. for seven days. Scale bar, 10 microns. (B) The mold phase of the mutant 4-2-2 is sensitive to calcofluor and Congo red. Mold of the mutant and the parental strain T53-19 were spotted inside a "race" tube containing solid 3M medium with the addition of either 20 µg/ml calcofluor (CF) or Congo red (CR), as described in the supplementary methods. Linear growth was measured over 60 days.

Figure 6:
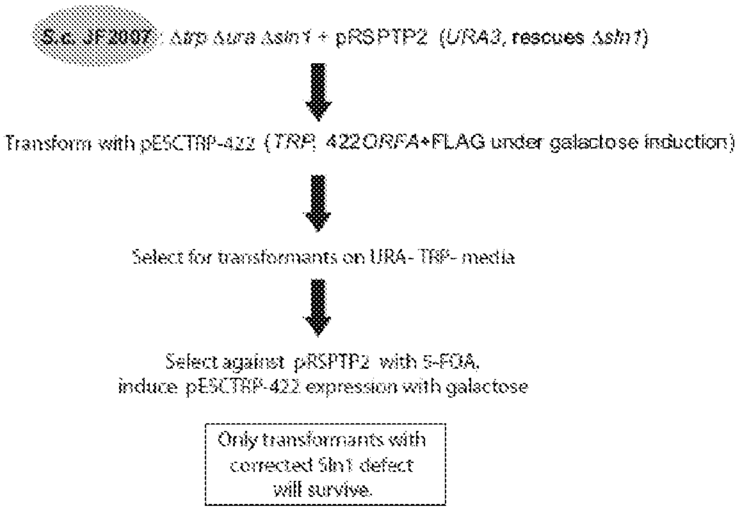
Figure 6:
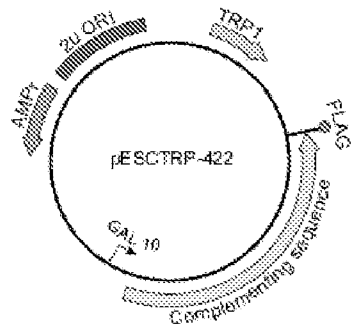

FIG. 6. Complementation of an SLN1 defect in *S. cerevisiae*. (A) *S. cerevisiae* strain JF2007 (sln1:LEU2, ura3-52, trp1Δ63, his3Δ200, leu2Δ1, lys2, pRSPTP2 [URA3]) is rescued from a lethal sln1 defect by a plasmid containing PTP2. JF2007 was transformed with an expression vector containing either SLN1 (pGalSln1) or the putative *Blastomyces* histidine kinase sequence (pESCTRP-422). Transformants were selected on media lacking uracil and tryptophan. Transformants were patched on media containing 5-FOA to select against maintenance of the PTP2-containing plasmid. Transformants receiving the *Blastomyces* putative histidine kinase survived the loss of PTP2, indicating that the *Blastomyces* sequence rescued an sln1 defect. (B) Expression vector pESCTRP-422 contains the ORFA complementing sequence with a FLAG tag under the control of the *S. cerevisiae* galactose-inducible promoter Gal10. The vector contains an ampicillin-resistance marker (AMPr), a 2µ yeast origin of replication (2µ ORI), and a yeast TRP1 selection marker (TRP1). Vector backbone is pESC-TRP (Stratagene, La Jolla, Calif.).

Figure 7:
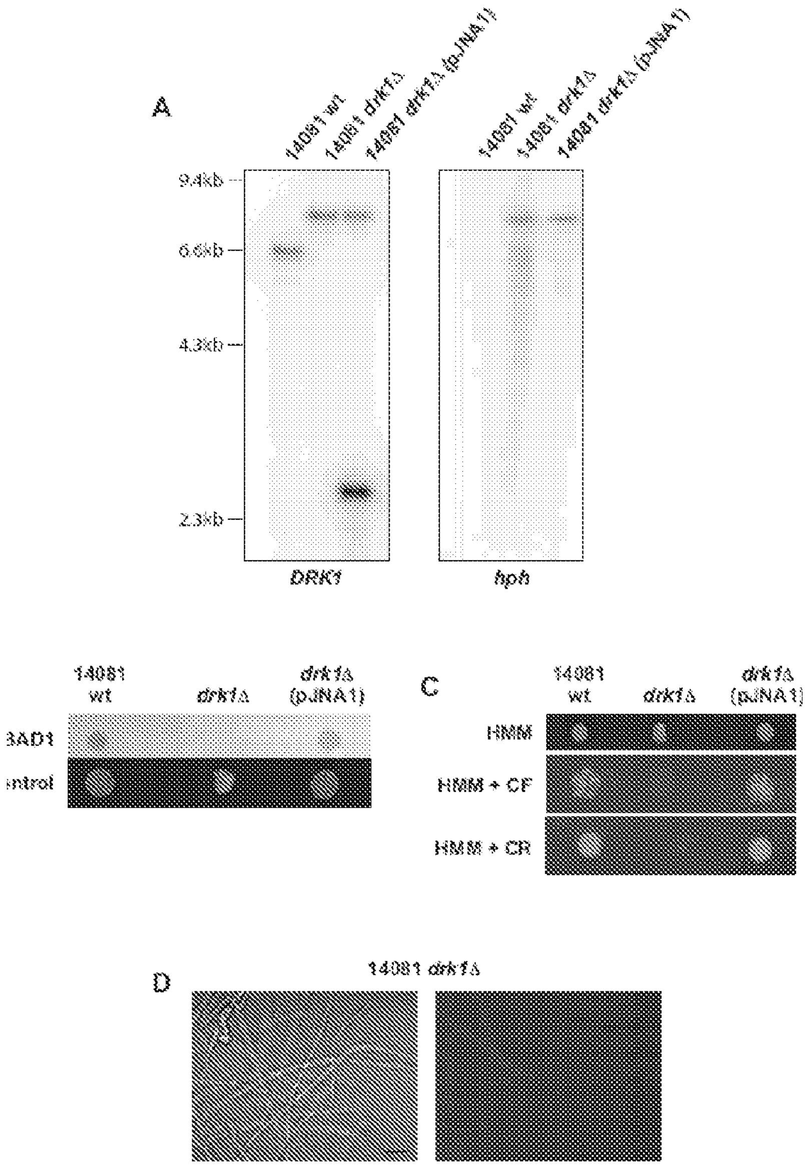

FIG. 7. DRK1 gene disruption in *B. dermatitidis*. (A) Southern analysis. Genomic DNA was isolated from wild-type strain 14081 and the isogenic knockout (drk1Δ; strain 14081-21-1) and complemented strains (drk1Δ (pJNAI); strain 14081-21-1-2) and digested with Sal I. This enzyme restricts the 3825 bp open reading frame of the gene 3050 bp from the translation start site. Restriction digests were separated by electrophoresis and blotted for Southern analysis. Blots were hybridized separately with two radiolabelled probes: a 822-bp fragment of the hygromycin phosphotransferase gene (hph) or a 952-bp fragment of the *Blastomyces* histidine kinase DRK1 from the 3' end of the open reading frame. Both probes were generated via PCR. In the wild-type strain, the DRK1 probe (left panel) hybridizes to the native DRK1 locus on a 6.6 kb Sal I fragment. In the DRK1-knockout, this DRK1 probe hybridizes to the hph-disrupted locus on a larger 7.7 kb Sal I fragment. In the complemented strain, this probe hybridizes to both the 7.7 kb fragment containing the disrupted locus, and a new 2.5 kb Sal I fragment containing the intact copy of DRK1 expressed ectopically in trans. The hph probe (right panel) hybridizes only to the hph-disrupted DRK1 locus on the 7.7 kb Sal 1 fragment, but not to the native DRK1 locus on the 6.6 kb fragment, or to the ectopically expressed DRK1 locus (selected with nourseothrecin) on the 2.5 kb fragment, as expected. (B) BAD1 expression. BAD1 was detected with mAb DD5-CB4 in a fungal colony overlay as described in the supplemental methods. Strains are wild-type and isogenic drk1Δ and complemented strains. The cell patch stained for BAD1 is shown below. (C) Sensitivity to cell wall active agents. Strains were plated at a density of 2×106 cells per ml and tested for growth over three days on HMM alone (control) or containing 20 µg/ml calcofluor (CF) or Congo red (CR). Strains are wild-type and isogenic drk1Δ and complemented strains. (D) Surface α-(1,3)-glucan. Cells were stained with mAb MOPC104e and goat anti-mouse fluorescein isothiocyanate. Light image is shown to the left of fluorescent image. Scale bar, 10 microns.

Figure 8:
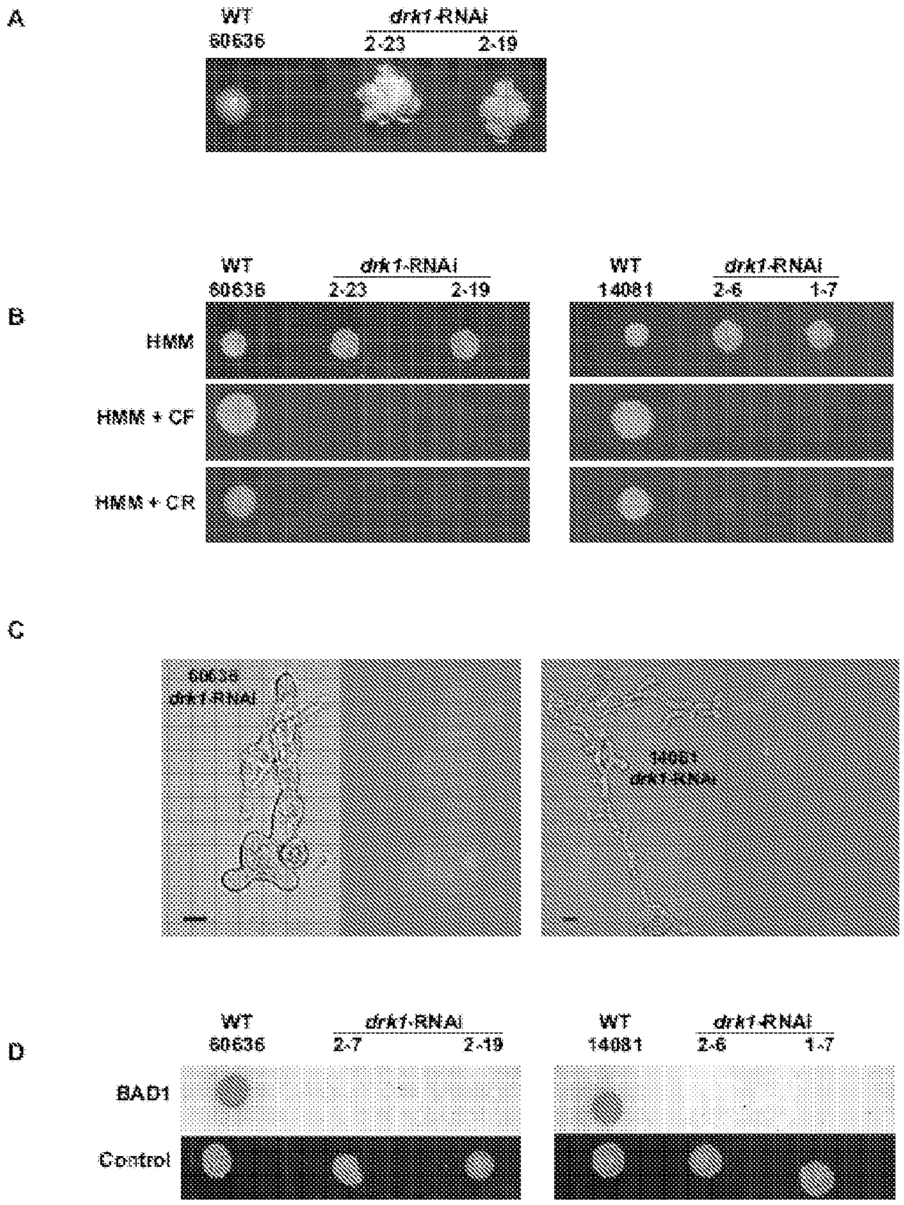

FIG. 8. Additional phenotypes of DRK1-silenced transformants in *B. dermatitidis*. (A) Surface morphology of wild-type *B. dermatitidis* strain 60636 and DRK1-silenced strains of (60636-2-23, 60636-2-19). Isolates were grown on 3M medium for four days and their surface morphology assessed. (B) Sensitivity of DRK1-silenced strains to cell wall active agents calcofluor (CF) or Congo red (CR). Wild-type and DRK1-silenced strains (2×106 cells/ml) were grown for three days on HMM alone or containing 20 µg/ml of either calcofluor or Congo red. (C) Surface α-(1,3)-glucan on DRK1-silenced strains. Cells were stained with mAb MOPC104e and goat anti-mouse fluorescein isothiocyanate. Light image is shown to the left of fluorescent image. Scale bar, 10 microns. (D) BAD1 expression. Fungal colony overlay was done as described in the supplemental methods. BAD1 was detected with mAb DD5-CB4. The cell patch stained for BAD1 is shown below.

Figure 9:
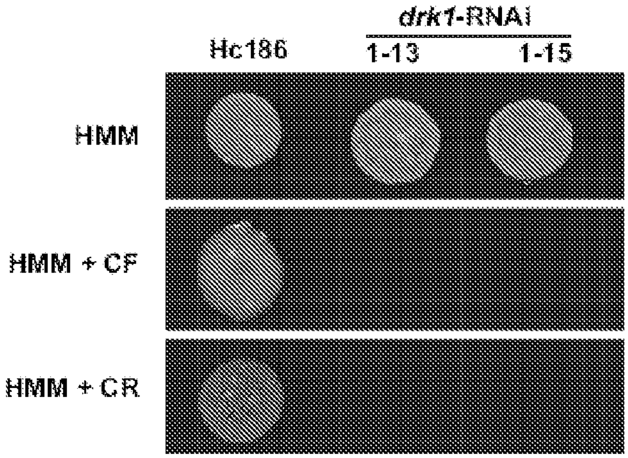
Figure 9:
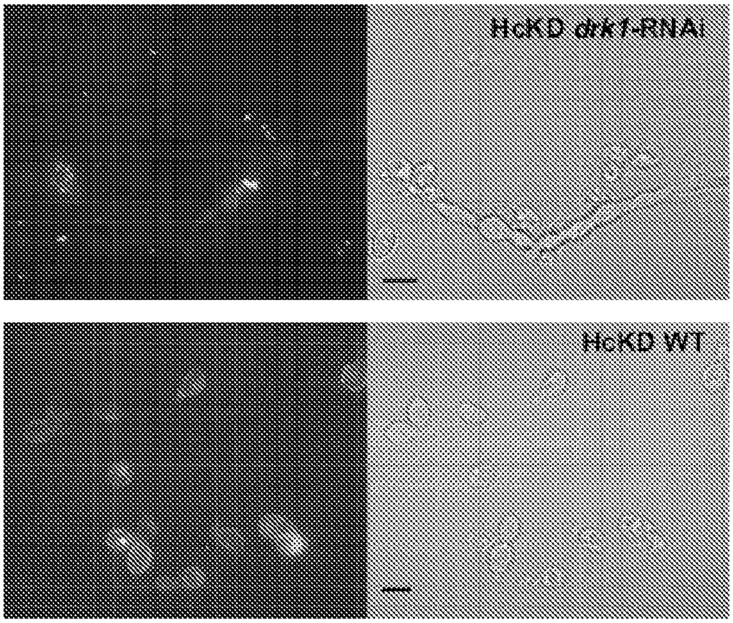

FIG. 9. Additional phenotypes of DRK1-silenced transformants in *H. capsulatum*. (A) Sensitivity of DRK1-silenced strains to cell wall active agents. Parental strain 186ARura5 and DRK1-silenced strains of (186-1-13 and -1-15). 2×106 cell/ml were grown for three days on HMM alone or containing either 20 µg/ml calcofluor (CF) or Congo red (CR). (B) Surface α-(1,3)-glucan. Cells were stained with mAb MOPC104e and goat anti-mouse isothiocyanate. Light image is shown to the right of fluorescent image. Scale bar, 10 microns.

FIG. 10. Virulence of DRK1-silenced transformants of *B. dermatitidis*. Mice were infected intratracheally as described in the examples (FIG. 4). The wild-type and DRK1-silenced strains of *B. dermatitidis* are the same as depicted in FIG. 4, as described above, except they were inoculated at 100-fold higher doses in this experiment (106 spores).

Figure 11:
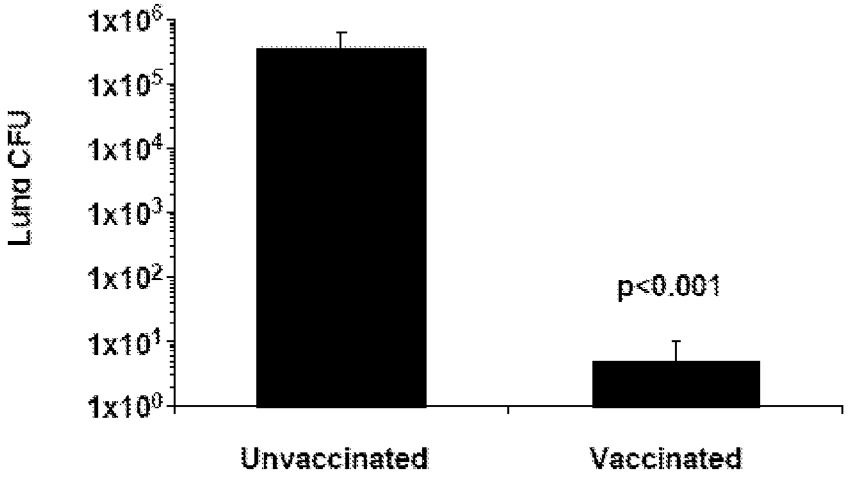

FIG. 11 is a bar graph comparing mice vaccinated and unvaccinated with DRK1-silenced yeast.

DESCRIPTION OF THE INVENTION

Dimorphic fungi are ubiquitous in the environment and harmless. Once inhaled, however, the organisms can morph into virulent yeast and cause life-threatening conditions, such as pneumonia and meningitis. The six species of dimorphic fungi—*Blastomyces dermatitidis, Histoplasma capsulatum, Coccidioides immitis, Paracoccidioides brasiliensis, Sporothrix schenckii*, and *Penicillium marneffei*—are all potentially pathogenic.

Survival after dimorphic fungal infections depends on the stage of detection and the subsequent effectiveness of treatment. Current treatment includes use of general anti-fungals that target disruption of cell membrane. These treatments suffer from toxicity and inadequate efficacy. Some patients will mount an immune response that forces the organism into remission, but the body typically does not clear the mold which lies dormant until a stress event triggers morphogenesis into the virulent yeast. This phenomenon is seen in AIDS patients who are highly susceptible to infection by these organisms due to their compromised immune system.

Nemecek et al., (*Science,* 312, 583, (Apr. 12, 2006), incorporated by reference) discloses aspects of the present inven tion and describes the inventors' work in the discovery of a global regulator of morphogenesis and pathogenicity in dimorphic fungi. In brief, the inventors have identified the gene responsible for the transformation of these organisms from harmless mold into virulent yeast. By analysis of a mutant with regulatory defects, the inventors have identified an open reading frame encoding a protein of 1274 residues displaying homology to domains of histidine kinase by BLAST Analysis and CD search. The inventors have confirmed their observation by using RNA interference (RNAi) for gene silencing in *B. dermatitidis* and *H. capsulatum.*

In one embodiment, the present invention is a method of determining whether a compound is an anti-fungal reagent by determining whether the compound inhibits activity of the fungal histidine kinase. By "fungal histidine kinase", we mean the *B. dermatitidis* kinase named "DRK1" for Dimorphism Regulating Kinase and its homologues. This gene now has an accession number at GenBank (DQ420627) and is provided at SEQ ID NO:1. The DQ420627 sequence for DRK1 was generated as part of a genome sequencing project unrelated to Nemecek, et al., 2006 Supra. It has about 10 nucleotide errors, compared to the DRK1 sequence that we generated while confirming the sequence this gene (SEQ ID NO:1). Consequently, a putative second intron predicted by DQ420627 to be present at the 3' end of the coding region is not actually present. DRK1 has a high degree of sequence identity to homologues from the other dimorphic fungi. For example, it is about 90% identical to the DRK1 homologue from *H. capsulatum.*

By "homologues", we mean that the dimorphic fungi gene encodes a histidine kinase, that all of the critical domains of the histidine kinase are present, and that the conventional organization of the domains structurally is present, i.e. A, B, C, D are all present, and B follows A, C follows B, etc. (See Ann. Rev. Biochem 2000:69:183-215 for description of domains.) An H-box and D-box must be present; N-and G-boxes for ATP binding and catalytic function, respectively, are preferably present, and would helping assigning function. There is often a good deal of sequence variability in the regions between the functional domains, so the overall homology of the gene may be a good deal lower than 80% to DRK1. Specifically, we refer to fungal histidine kinases found in *C. immitis* (genome sequence has a GenBank accession number of: AAEC01000000) and *H. capsulatum* (the Whole Genome Shotgun project has been deposited at DDBJ/EMBL/GenBank under the project number: AAJI00000000). One of skill in the art would be able to identify the homologue kinases: for example, on the NCBI website, for *H. capsulatum* strain NAml, the contig number is 1.1287. On the NCBI website, for *C. immitis* strain RMSCC 2394, the contig number is 1.151; for *C. immitis* strain H538.4, the contig number is 1.1981; and for *C. immitis* strain RS, the contig number is 2.24.

One would expose a test compound to a sample of the fungal histidine kinase, preferably DRK1, and determine whether the kinase has loss of activity. A molecular compound that shows inhibition will be a strong compound for further testing as an anti-fungal. Preferably, one would then test successful compounds against dimorphic fungi in vitro.

We predict that the compounds of the present invention will be successful against the six species of dimorphic fungi, listed above, and will also be effective against other classes of pathogenic fungi. Two-component regulatory systems (similar to the one described herein for *B. dermatitidis*) have been described in members of all the kingdoms of life. These sensor-regulator pairs govern vital biological processes including morphogenesis in simple animals such as slime mold, expression of virulence genes in bacterial pathogens such as *Bordatella pertussis* (the cause of whooping cough) and the developmental behavior of spores of bacteria such as members of the family that cause anthrax.

Histidine kinases have been identified in other pathogenic fungi such as *Candida albicans, Cryptococcus neoformans*, and *Aspergillus fumigatus*. In *Candida*, they are important in control of cell shape, cell wall integrity, and survival in the mammalian host. In *Cryptococcus*, they are also important in sensing environmental change and survival under harsh conditions. Histidine kinases are present in *Aspergillus* and are currently under study.

Because of the vital role of histidine kinases in fundamental programs of fungi relating to the sensing of environmental change/stress and the appropriate response to it such as maintenance of cell wall integrity and expression of resistance genes (i.e. virulence in mammalian hosts), we propose that turning off these sensor-responder systems will behave the same as in dimorphic fungi.

A preferred protocol for a high-throughput screen for anti-fungal compounds follows: We intend to perform high-throughput screening for compounds or small molecules that inhibit the function of a conserved fungal histidine kinase present in the dimorphic fungi. We have observed that the Promega KINASE-GLO LUMINESCENT KINASE Assay reliably records activity of the histidine kinase in vitro by providing a luminescent signal that is correlated (inversely) with the amount of ATP present in the assay. The assay can be done in 96-or 396-well microtiter well plates by adding the fungal histidine kinase, ATP and the KINASE GLO REAGENT provided by Promega in the luminescent assay kit. After incubation, signal is read in a luminometer. Luminescent output is inversely correlated with kinase activity. The KINASE GLO REAGENT relies on the presence of thermostable luciferase to produce a luminescent signal that is stable for a half-life of over 4 hours. This feature allows for batch mode processing of multiple plates, which is ideal for high-throughput screening.

We have used the above assay to biochemically establish kinase activity of the fungal histidine kinase in question. We will format the assay for high-throughput screening of chemical libraries in the Keck Small Molecule Facility, U. Wisconsin, Madison, Wis. Briefly, we will screen several of their libraries containing more than 40,000 small molecules and compounds for those that interfere with the kinase activity of the fungal histidine kinase. Robots will be used to introduce individual test molecules and compounds into the wells of plates containing the kinase, ATP, and KINASE-GLO REAGENT.

Preferably, the amounts of material added to the wells are as follows:

To each well:

1. Add 50 ul kinase slurry in buffer, 1:2 dilutions across 96 well plate and ATP to 6.5 uM.
2. Incubate 2 hours at room temperature.
3. Add 50 ul KINASE-GLO reagent then incubate 10 minutes at room temperature.
4. Measure luminescence immediately.

After incubation with a test compound in question, the loss of luminescent signal will indicate that the kinase is active and that the compound did not inhibit the kinase. In contrast, strong luminescent signal will suggest that a compound interfered with activity of the kinase in the reaction.

A molecule or compound that shows initial activity in the assay—that is, inhibits kinase activity—will be tested in more depth individually over a range of concentrations in vitro to identify that concentration needed to inhibit 50% of the kinase activity i.e. $IC_{50}$. If a compound shows strong potency against the kinase, it will be tested for activity over a range of concentrations against dimorphic fungi (and perhaps other classes of pathogenic fungi) in vitro. Promising compounds in these in vitro assays will be investigated in animal models of systemic fungal infection that are currently in use in the laboratory, to define those that have therapeutic promise for treating systemic fungal infections.

Of course, one of skill in the art may wish to examine the activity of candidate compounds against fungal histadine compounds against alternative ways. For example, one may wish to examine the compound in an in vivo fungal model before any other consideration. One may wish to put the histadine kinase gene into a model yeast system and demonstrate inhibition in that way.

In another embodiment, the present invention is a strain of dimorphic fungi wherein the fungal histidine kinase regulating morphogenesis and pathogenicity has been inactivated. The examples describe at least three ways of making such stains. The examples describe a genetically engineered fungi, wherein the alteration resides within ORFA of *B. dermatitidis* and also describe the creation of an RNA inactivated fungi by the application of RNAi in two different *B. dermatitidis* strains. The examples also demonstrates the use of RNAi with an *H. capsulatum* and a clinical isolate, HCKD.

A common and preferable way of making non-morphing fungi of the present invention would be to make a "knockout" in the gene. This is typically done by targeting the gene of interest and disrupting it. Typically, one delivers a defective copy of the gene of interest into the organism. That copy integrates into the chromosome of the fungus, where it replaces the healthy gene copy, leaving the fungus with the defective copy. One then confirms this gene replacement event, typically by analyzing the chromosomal DNA and examines the functional consequences. This would be the standard or preferred method, when possible, rather than random mutagenesis or RNAi. The examples demonstrate this method. The gene sequence of homologues can be found at GenBank.

In another embodiment, the present invention is the use of the non-virulent organism as a vaccine or to develop a vaccine. U.S. Pat. No. 6,248,322 describes an attenuated vaccine for *B. dermatitidis*. The vaccine strain is the DRK1 knockout (or silenced) strain of the fungus. Its advantage is that it is no longer virulent, but still highly immunogenic and protective against re-challenge with a wild-type virulent strain that is genetically related or unrelated to the vaccine strain. Generally, one gives the vaccine twice subcutaneously, 50,000 yeast at each of two sites, for a total of 100,000 live attenuated organisms.

EXAMPLES

Example I

Global Control of Dimorphism and Virulence in Fungi

BAD1 of *B. dermatitidis* was used as "bait" in hunting for regulators of dimorphism because it is expressed during the transition to yeast, regulated transcriptionally, and required for pathogenicity (P. J. Rooney, T. D. Sullivan, B. S. Klein, *Mol Microbiol* 39, 875 (2001); T. T. Brandhorst, M. Wüthrich, T. Warner, B. Klein, *J Exp Med* 189, 1207 (1999).). To identify mutants with regulatory defects, we created a *B. dermatitidis* reporter strain T53-19 harboring a transcriptional fusion between the BAD1 promoter and β-galactosidase reporter, $P_{BAD1}$-LacZ. We transformed T53-19 with *A. tumefaciens* and monitored regulatory defects using a color screen (Materials and methods are available as supporting material on Science online.). As yeast at 37° C., the reporter strain stains blue on media containing 5-bromo-4-chloro-3-indolyl-beta-D-galactoside (X-gal). As mold at 22° C., it fails to stain and is white. Since BAD1 expression is upregulated in yeast, we sought mutants that were white instead of blue at 37° C. In screening ≈15,000 transformants, we found seven with color defects. These transformants were confirmed by colony immunoblot and Northern analysis to have diminished BAD1 and 7-to 105-fold reductions in transcript.

Figure 1:
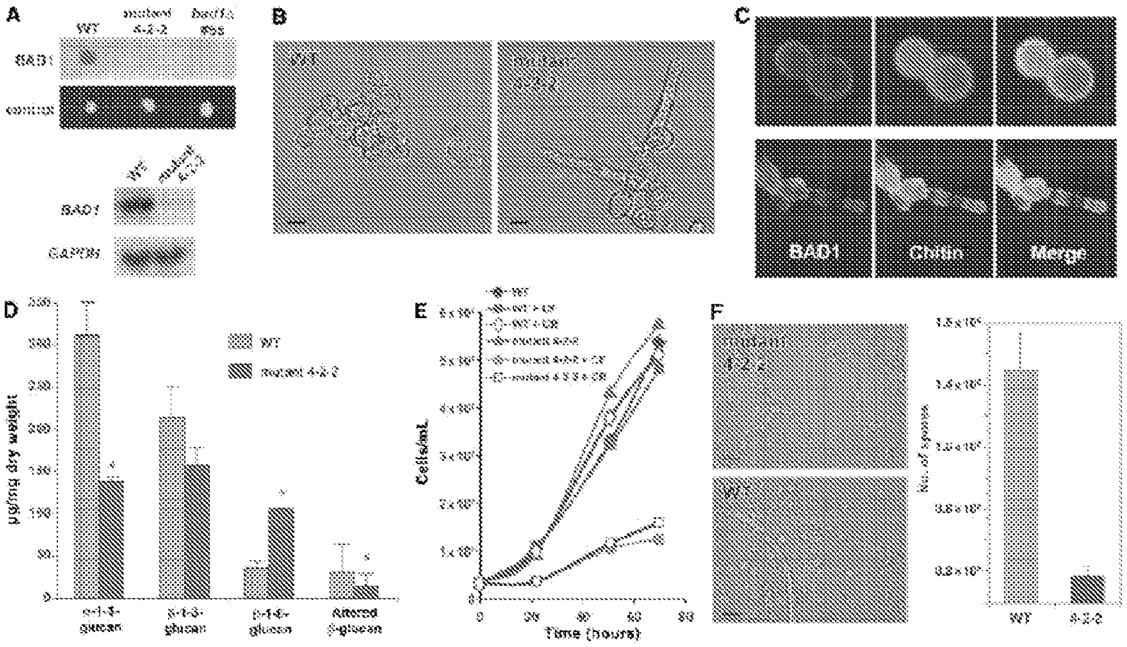
FIG. 1. An insertional mutant of *B. dermatitidis* with pleotropic defects in morphogenesis, virulence gene expression, cell wall integrity, and sporulation. (A) Top: fungal colony overlay and immunoblot for BAD1. Nitrocellulose overlay of colonies probed with anti-BAD1 mAb DD5-CB4. Parental reporter strain T53-19 (WT) is a positive control and bad1Δ strain 55, a negative control. The patches of fungal cells tested are shown below the blot. Bottom: Northern analysis. By densitometry, BAD1 transcript is 7-fold lower in mutant vs. WT. GAPDH, loading control. (B) Microscopic appearance of mutant and WT parent strain grown at 37° C. in liquid HMM. The mutant phenotype is stable on serial passage. Scale bar, 10 microns. (C) Surface BAD1 (red), chitin (green) and merged images. Top, WT; bottom, mutant. BAD1 is stained with mAb DD5-CB4 and goat anti-mouse phycoerythrin; and chitin, with wheat germ agglutinin-fluorescein isothiocyanate. (D) Cell wall composition. Cell walls were obtained and analyzed as described. The mutant has two-fold less α-1-3 glucan and 3-fold more β-1-6 glucan vs. the WT strain. $^*p<0.05$, ANOVA test. Data are mean ±SD of three experiments. (E) Sensitivity to the cell wall binding agents calclofluor (CF) and Congo red (CR). Growth at 37° C. of WT reporter strain and mutant was analyzed in liquid HMM alone or with CF or CR (20 μg/ml). Growth rate was quantified by counting cells/ml. Data from one representative experiment of three is shown. Results were similar at 22° (FIG. 5B). (F)

One mutant, 4-2-2, had a 7-fold reduction in BAD1 transcript, corresponding reduction in BAD1 (FIG. 1A), and pleotropic defects. At 37° C., 4-2-2 fails to convert to yeast and grows as pseudohyphae (FIG. 1B). Cell wall composition is altered in the mutant (FIGS. 1C and D). BAD1 and chitin are distributed in an aberrant striated pattern in the cell wall and the amount of α-(1,3)-glucan is greatly reduced. As evidenced in other cell-wall mutants (J. M. van der Vaart, et. al., *J Bacteriol* 177, 3104 (1995).), mutant 4-2-2 is more sensitive than the parent strain to the cell-wall-binding chemicals calcofluor and Congo red (FIG. 1E). After sporulation, mutant 4-2-2 produces nearly 10-fold fewer conidia (the infectious particles) than the parental strain (FIG. 1F), and spore progeny of the mutant retain a pseudohyphal phenotype when grown at 37° C. (FIG. 5). Despite these pleotropic defects, the mutant grows at the same rate as the parent strain (Table 1). Mutant 4-2-2 thus possesses global defects in morphogenesis, cell wall composition, sporulation and expression of virulence factors BAD1 and α-(1,3)-glucan.

TABLE 1

Growth rate (doubling time) of strains studied*.

| Isolate | Doubling time (hrs.) |
|---|---|
| *Blastomyces dermatitidis* | |
| T53-19 (reporter strain) | 17.86 ± 0.12 |
| Mutant 4-2-2 | 18.20 ± 0.88 |
| Strain 14081 (wt) | 17.56 ± 0.57 |
| 14081-2-6 (drk1RNAi) | 16.56 ± 0.09 |
| 14081-1-7 (drk1RNAi) | 17.32 ± 0.26 |
| 14081-1-12 (drk1RNAi) | 18.27 ± 0.21 |
| ATCC 60636 (wt) | 17.44 ± 0.53 |
| 60636-2-7 (drk1RNAi) | 16.58 ± 0.40 |
| 60636-2-19 (drk1RNAi) | 16.15 ± 0.85 |
| 60636-2-23 (drk1RNAi) | 17.27 ± 0.11 |
| *Histoplasma capsulatum* | |
| Strain KD (wt) | 9.88 ± 0.12 |
| KD-6 (drk1RNAi) | 9.35 ± 0.02 |
| KD-15 (drk1RNAi) | 10.64 ± 0.06 |
| KD-10 (drk1RNAi) | 8.94 ± 0.02 |

*Wild-type strains were from ATCC when noted, or from patients. Data represent the mean and standard deviation of results from two independent experiments.

By Southern analysis, we determined that T-DNA had inserted into one site in the genome of mutant 4-2-2. By adapter polymerase chain reaction (PCR), 256 and 412 nucleotides flanking 5' and 3' of the T-DNA insertion, respectively, were amplified and sequenced. Flanking sequence showed identity to contig 52 in the *Blastomyces* genome (*GSC BLAST Search*.). Two large putative ORFs (*ORFA* and *ORFB*) were identified near the insertion site (FIG. 2A). The T-DNA transected *ORFA*, whose transcript is not detectable in mutant 4-2-2 by Northern analysis (FIG. 2B). To assess the functional role of these ORFs in mutant 4-2-2, we complemented the strain with a gene copy of *ORFA* or *ORFB* (FIG. 2B). A plasmid containing an intact genomic copy of *ORFA* and flanking sequence reversed the phenotypic defects in the mutant (FIG. 2C), whereas that containing *ORFB* and flanking sequence did not.

ORFA encodes a protein of 1274 residues based on transcript size and predicted by gene-finding software (Softberry, Mount Kisco N.Y.). The gene has three exons totaling 3825 base-pairs and two introns of 140 and 40 basepairs, and displays homology to domains of histidine kinase by BLAST analysis and CD-search. Histidine kinases are signal transduction proteins that organisms in all three domains of life use to respond to environmental signals (S. Li et al., *Embo J* 17, 6952 (1998).) and control developmental processes (L. A. Alex, C. Korch, C. P. Selitrennikoff, M. I. Simon, *Proc Natl Acad Sci USA* 95, 7069 (1998); T Yamada-Okabe et al., *J Bacteriol* 181, 7243 (1999).). ORFA is predicted to have two trans-membrane domains and the necessary elements for histidine kinase function, including the histidine-containing H-box and aspartate-containing D-box involved in phosphorelay (FIG. 2D). The sequence also contains the N and G boxes used in ATP-binding and catalytic function, and an aspartate-containing receiver domain. The *B. dermatitidis* sequence is homologous to the hybrid histidine kinase SLN1 in *Saccharomyces cerevisiae* and to sequences in the genomes of *H. capsulatum* and *C. immitis*, dimorphic fungi for which extensive genome sequence is available (FIG. 2D).

We assayed the histidine kinase activity of ORFA using genetic and biochemical approaches. The ORFA of *B. dermatitidis* was expressed heterologously in *S. cerevisiae* to see if it functionally complements an sln1 defect in strain JF2007 (I. M. Ota, A. Varshavsky, *Science* 262, 566 (1993).). *S. cerevisiae* possesses a single hybrid histidine kinase, Sln1p, which regulates an osmosensing MAP kinase cascade, an oxidative stress response pathway, and cell-wall biosynthesis (T. Maeda, A. Y. Tsai, H. Saito, *Mol Cell Biol* 13, 5408 (1993); B. Krems, C. Charizanis, K. D. Entian, *Curr Genet.* 29, 327 (1996).). The lethal sln1 defect in JF2007 is viable due to the presence of a plasmid containing the phosphatase gene PTP2. Ptp2p dephosphorylates the Hog1 protein that accumulates in the absence of the functional histidine kinase (A. Winkler et al., *Eukaryot Cell* 1, 163 (2002).). After lithium acetate transformation of JF2007 with an expression vector containing either ORFA or SLN1, we selected against maintenance of the PTP2 transgene via growth on 5-fluoroorotic acid (5-FOA). Transformants receiving either SLN1 or ORFA survived the loss of PTP2, implying that ORFA functionally complements the sln1 defect (FIG. 2E, and FIG. 6). In biochemical studies, the *B. dermatitidis* ORFA protein product, immunoprecipitated from *S. cerevisiae* transformants, exhibited histidine kinase activity similar to Sln1p in a luminescent assay (FIG. 2F). ORFA thus encodes a protein that functions genetically and biochemically as a histidine kinase.

To unambiguously test the role of *B. dermatitidis* histidine kinase in the global defects observed in mutant 4-2-2, we created a targeted knockout by allelic replacement (FIG. 7A). The knockout is locked in the mold form at 37° C. (FIG. 3A) and has all of the pleotropic defects of mutant 4-2-2 (impaired BAD1 and α-(1,3)-glucan expression, sensitivity to calcoflour and Congo red, and failure to sporulate)—to a more extreme extent (FIG. 7B-D). Complementing the knockout corrected these defects (FIG. 3A, and FIG. 7). Henceforth, we refer to the gene here as DRK1 for Dimorphism Regulating histidine Kinase. We were unable to test virulence of DRK1 knockout strains in mice because the hyphae could not be reliably quantified and no spores were made. The more severe phenotype of the knockout compared to the insertion mutant 4-2-2 suggests that there is residual gene activity in the latter, perhaps due to the partial function of a truncated protein, or to minimal DRK1 transcript beneath the level of detection.

We exploited RNA interference (RNAi) for gene silencing in *B. dermatitidis* to knock down DRK1 function and circumvent the extreme phenotypes of the knockout (14). RNAi experiments were carried out in two different *B. dermatitidis* strains: 60636, and 14081. DRK1-silenced transformants from all three strains exhibit rough colony morphology and pseudohyphal growth at 37° C., reduced sporulation, and sensitivity to calcoflour and Congo red (FIG. 3B; and FIG. 8 and Table 2). To explore the relationship between *B. dermatitidis* DRK1 and expression of yeast-phase virulence genes, we analyzed transcript for DRK1, BAD1 and AGS1 by Northern analysis in DRK1-silenced strains. BAD1 and AGS1 transcripts are absent in parallel with that of DRK1, and the transcript for BYS1, a yeast-phase gene of unknown function, is inconsistently reduced in the strains (FIG. 3B).

TABLE 2

Impaired sporulation of *B. dermatitidis* and *H. capsulatum* after gene silencing of DRK1.

| Isolate | Spores/mL | Fold reduction* |
|---|---|---|
| *Blastomyces dermatitidis* | | |
| 14081 (wt) | $1.9 \times 10^6$ | n/a |
| 14081-2-6 (drk1RNAi) | $7.2 \times 10^4$ | 27.3 |
| 14081-1-7 (drk1RNAi) | $7.6 \times 10^4$ | 25.7 |
| 14081-1-12 (drk1RNAi) | $5.8 \times 10^4$ | 33.9 |
| 60636 (wt) | $1.7 \times 10^6$ | n/a |
| 60636-2-7 (drk1RNAi) | $1.3 \times 10^4$ | 12.5 |
| 60636-2-19 (drk1RNAi) | $5.9 \times 10^4$ | 27.5 |
| 60636-2-23 (drk1RNAi) | $4.1 \times 10^4$ | 40.2 |
| *Histoplasma capsulatum* | | |
| Strain KD (wt) | $1.5 \times 10^8$ | n/a |
| KD-6 (drk1RNAi) | $1.1 \times 10^7$ | 14.4 |
| KD-15 (drk1RNAi) | $1.1 \times 10^7$ | 13.9 |
| KD-10 (drk1RNAi) | $1.3 \times 10^7$ | 12.0 |

*Fold reduction of strain compared to results for the parental isolate.

The DRK1 sequence and its key domains are highly conserved in *H. capsulatum* and *C. immitis* (FIG. 2D). To test whether DRK1 acts as a global regulator of dimorphism and yeast-phase virulence gene expression in other dimorphic fungi, we used RNAi to silence gene expression in *H. capsulatum*. DRK1 was silenced in strain 186ura5AR and a clinical isolate, HcKD (Materials and methods are available as supporting material on Science online.). Transformants were initially screened for those that grew as pseudohyphae at 37° C. DRK1-silenced strains showed concomitant reduction in the expression of virulence factors CBP1 and α-(1,3)-glucan (9, 24), sensitivity to calcoflour, and reduced sporulation (FIG. 3C; and FIG. 9 and Table 2). Transcript levels for the silenced strains were correspondingly reduced for DRK1, CBP1 and AGS1 (FIG. 3C). Strikingly, the brown pigment indicative of melanin in mycelia and spores of wild type *Histoplasma* strains was absent in the DRK1-silenced strains (FIG. 3D). Melanin is linked with virulence in other fungal pathogens, including *C. neoformans* and *A. fumigatus* (J. D. Nosanchuk, A. Casadevall, *Cell Microbiol* 5, 203 (2003).). The histidine kinase DRK1 thus regulates global functions, including dimorphism and virulence gene expression in *H. capsulatum.*

Since mold-to-yeast transition and expression of the yeast phase genes BAD1, CBP1 and AGS1 are required for pathogenicity, we postulated that silencing DRK1 expression would impair virulence of *B. dermatitidis* and *H. capsulatum*.

We investigated virulence of DRK1-silenced strains in a mouse model of lethal pulmonary infection. After intra-tracheal infection with spores of *B. dermatitidis*, DRK1-silenced strains from two independent isolates were sharply attenuated compared to wild-type strains, as measured by survival and lung colony-forming units (CFU) (FIG. 4A). In a murine model of histoplasmosis following intra-tracheal infection with spores, DRK1-silenced strains of *H. capsulatum* also were sharply reduced in virulence compared to wild-type strains (FIG. 4B). The growth rate of DRK1-silenced strains in all genetic backgrounds was similar to that of the respective parent strain (Table 1). Silencing expression of the histidine kinase DRK1 therefore reduced pathogenicity markedly in two dimorphic fungi.

We have described a highly conserved hybrid histidine kinase DRK1 that is indispensable for dimorphism, virulence gene expression, and pathogenicity in dimorphic fungi. Our finding that DRK1 gene disruption locks a dimorphic fungus in the mold form uncovers a long-sought regulator of phase transition. The observation that phase-locked cells lose virulence extends the biochemical studies of Medoff et al (G. Medoff et al., *Science* 231, 476 (1986).) and offers genetic proof that conversion of mold to yeast is required for pathogenicity in dimorphic fungi. A change in shape alone probably does not explain why the conversion is required, since mold and yeast differ in the expression of many genes and phenotypes, including some that are linked with virulence.

Two-component signaling systems are widespread in the prokaryotes. Eukaryotes have been thought to rely mainly on serine, threonine and tyrosine kinases for signal transduction, but histidine kinase two-component systems have recently been shown to play a role in environmental sensing and cell development in eukaryotes (J. L. Santos, K. Shiozaki, *Sci STKE* 2001, RE1 (2001).), including in *Candida albicans* where they regulate filamentation (L. A. Alex, C. Korch, C. P. Selitrennikoff, M. I. Simon, *Proc Natl Acad Sci USA* 95, 7069 (1998); T Yamada-Okabe et al., *J Bacteriol* 181, 7243 (1999).). We show that a histidine kinase regulates sensing of environmental changes needed for mold-to-yeast transition in at least two dimorphic fungal pathogens. Histidine kinase homologs were identified in three dimorphic species for which the most complete genome sequence is available: *B. dermatitidis, H. capsulatum*, and *C. immitis*. The presence of this gene in multiple species, and its conserved role in *B. dermatitidis* and *H. capsulatum*, suggests that it may control phase transition and virulence gene expression, as well as cell-wall development and sporulation, in the other systemic dimorphic fungi. DRK1 shares limited sequence similarity to histidine kinases that regulate filamentation in the more distantly related fungus *C. albicans*, although the functional domains are conserved. Nevertheless, the finding that histidine kinases regulate changes in shape for diverse fungal species points to a potentially broad role of these environmental sensors in the fungal kingdom.

What is the environmental signal that DRK1 of *Blastomyces* and *Histoplasma* senses to regulate phase transition and virulence gene expression? In *S. cerevisiae*, Sln1p detects osmotic stress, whereas in *Schizosaccharomyces pombe*, the histidine kinase-regulated SPC1 MAPK cascade senses osmotic stress, as well as oxidative and heat stress and nutrient deprivation (J. C. Shieh, M. G. Wilkinson, J. B. Millar, *Mol Biol Cell* 9, 311 (1998).). Potential signals for histidine kinase sensing in dimorphic fungi include temperature, osmotic or oxidative stress, nutrient deprivation, redox potential, and host-derived factors such as hormones like 17-β-oestradiol, which induces germ tubes in *C. albicans* (S. White, B. Larsen, *Cell Mol Life Sci* 53, 744 (1997).) and blocks mold-to-yeast transition of *P. brasiliensis* (M. E. Salazar, A. Restrepo, D. A. Stevens, *Infect Immun* 56, 711 (1988).).

In *S. cervisiae*, the hybrid histidine kinase S1n1p transfers a phosphoryl group to the histidine residue of the phosphotransfer (HPt) domain in Ypd1p (*F. Posas et al., Cell* 86, 865 (1996).). Ypd1p transfers a phosphoryl group to one of two response regulators, Ssk1p or Skn7p, which control MAPK cascades and gene expression. Ypd1p, Ssk1p, and Skn7p homologs are present in both the *Blastomyces* and *Histoplasma* genomes; three other putative histidine kinases also are present (*GSC BLAST Search*.) The four histidine kinases may sense different environmental signals that all lead through Ypd1p to the same output of morphogenesis and virulence gene expression. Alternatively, multiple downstream response regulators could respond to stimulation from Ypd1p, each controlling a distinct program involved in phase transition.

Histidine kinases linked with two-component relays have been identified in all three domains of life, but none have been established in any of the fully sequenced vertebrate genomes. The lack of such a homolog in humans suggests that these proteins may serve as antifungal drug targets. Previously identified bacterial histidine-kinase inhibitors have had general antifungal activity that is not kinase-specific, instead resulting in general membrane damage (R. J. Deschenes, H. Lin, A. D. Ault, J. S. Fassler, *Antimicrob Agents Chemother* 43, 1703 (1999)). Greater knowledge of eukaryotic histidine kinase function could assist in the development of better-targeted inhibitory compounds. Dimorphic fungi attenuated by knocking out histidine kinase might also be used for vaccination purposes.

Strains and Growth Conditions

*B. dermatitidis* strains 26199 and 60636 were obtained from the American Type Culture Collection (Rockville, Md.) (B. S. Klein, J. M. Jones, *J Clin Invest* 85, 152 (1990)). The spontaneous uracil auxotrophic strain ER-3ura5-s11 was isolated by 5-fluoroorotic acid selection of germinating spores (T. D. Sullivan, P. J. Rooney, B. S. Klein, *Eukaryot Cell* 1, 895 (2002)). *B. dermatitidis* patient isolate 14081 was obtained from the Wisconsin State Laboratory of Hygiene (Madison, Wis.). *Histoplasma capsulatum* strain 186ARura5 (C. A. Rappleye, J. T. Engle, W. E. Goldman, *Mol Microbiol* 53, 153 (2004)) was a gift from Bill Goldman (Washington University in St. Louis) and *H. capsulatum* strain "KD" was a fresh patient isolate provided by the clinical microbiology laboratory of the University of Wisconsin Hospital and Clinics.

Fungi were grown in *Histoplasma* macrophage medium (HMM) or 3M medium at 37° C. (P. L. Worsham, W. E. Goldman, *J Med Vet Mycol* 26, 137(1988)). For conversion to mold, fungi were grown on potato flake agar at 22° C. (M. G. Rinaldi, *J Clin Microbiol* 15, 1159 (1982)). Conidia were harvested after 2 weeks by adding 5 mL of phosphate buffered saline (PBS) to the agar plate and using a glass rod to dislodge the spores from hyphae (P. J. Rooney, T. D. Sullivan, B. S. Klein, *Mol Microbiol* 39, 875 (2001)).

*Agrobacterium tumefaciens* strain LBA1100 (A. Beijersbergen, A. den Dulk-Ras, A. Schilperoort, P. J. Hooykaas, *Science* 256, 1324 (1992)) was provided by C. van den Hondel (Leiden University, Leiden, The Netherlands).

Generation of the Reporter Strain

A uracil auxtrophic *B. dermatitidis* strain ER-3ura5-s11 was transformed via electroporation with plasmid pPJ31 linearized by a Nco I digestion. pPJ31 contains a transcriptional fusion of the full-length BAD1 promoter (1560 base pairs) in front of the β-galactosidase reporter LacZ and Podospora anserina URA5 for selection (P. J. Rooney, unpublished). Transformants were selected on 3M lacking uracil and containing 200 μM cefotaxime. The resultant reporter strain is designated T53-19.

Colony Immunoblot for BAD1 Expression

For each strain, a 10 μL volume of 2×106 cells/mL of suspension was spotted onto duplicate 3M plates. Cell patches were incubated overnight at 37° C. A sterile nitrocellulose membrane (Millipore, Billerica, Mass.) was laid over one patch plate. Both plates were then incubated for 48 hours. The membrane was lifted from the plate and excess cell material was rinsed off with 1× Tris-buffered saline (TBS). The membrane was blotted using the anti-BAD1 monoclonal antibody DD5-CB4 (8) in 1×TBS-0.05% Tween blocking solution. Goat anti-mouse IgG (H+L) alkaline-phosphatase conjugate (Promega, Madison, Wis.) was used as the secondary antibody and blots were developed using BCIP/NBT substrate (Promega, Madison, Wis.).

Immunofluorescence Staining for Surface α-(1,3)-Glucan

Immunofluorescence staining for α-(1,3)-glucan on the surfaces of *H. capsulatum* and *B. dermatitidis* was done using mAb MOPC104e (Sigma) reactive against the polymer, followed by goat anti-mouse fluorescein isothiocyanate as previously described (K. R. Klimpel, W. E. Goldman, *Infect Immun* 56, 2997 (1988); L. H. Hogan, B. S. Klein, *Infect Immun* 62, 3543 (1994)).

Mutagenesis of the Reporter Strain

Reporter strain T53-19 was transformed with *A. tumefaciens* strain LBA1100 carrying the binary plasmid pBTS165. pBTS165 contains the glyceraldehyde-3-phosphate dehydrogenase (gpdA) promoter from *A. nidulans* in front of hygromycin phosphotranferase (hph) for selection. Transformants were selected on 3M plates containing 100 μg/ml hygromycin and 200 μM cefotaxime; they were transferred to 3M plates containing 100 μg/ml of 5-bromo-4-chloro-3-indolyl-beta-D-galactoside (X-gal) for blue-white color screening at 37° C.

Complementation of Mutant 4-2-2

Two binary vectors were designed for use in *A. tumefaciens* transformation: pJNA1 contained ORFA as well as 216 bases of 3' flanking sequence and 975 bases of 5' flanking sequence; pJNB1 contained ORFB as well as 461 bases of 5' flanking sequence and 162 bases of 3' flanking sequence. Both plasmids contained nourseothricin acetyltransferase (nat1) behind the gpdA promoter for selection. Transformants were selected on medium containing 25 μg/ml of nourseothricin and 200 μM cefotaxime.

SLN1 Complementation System

*S. cerevisiae* JF2007 (sln1::LEU2, ura3-52, trp1Δ63, his3Δ200, leu2A1, lys2, pRSPTP2 [URA3]) was transformed with either expression vector pGalSln1 or pEscTrp422 using a lithium acetate protocol. pGalSln1 (a generous gift from Jan Fassler, University of Iowa) contains *S. cerevisiae* SLN1, with a c-myc tag, under the control of the *S. cerevisiae* galactose-inducible promoter Gal10. pESCTRP422 contains the ORFA complementing sequence, with a FLAG tag, under the control of the *S. cerevisiae* galactose-inducible promoter Gal10. The pESC-TRP backbone used to generate pESC-TRP422 is available from Stratagene (La Jolla, Calif.). Both vectors contain the yeast TRP1 ORF for selection on medium lacking tryptophan.

After lithium acetate transformation, yeast were plated on medium lacking uracil and tryptophan to select for those containing an expression vector. Transformants were plated on medium containing 5-FOA to select against the URA3-containing pRSPTP2, and galactose to induce expression of the complementing sequence. Transformants were also patched on non-inducing medium containing glucose and 5-FOA, and additionally on complete medium lacking 5-FOA as controls for growth. pRSPTP2 contains PTP2, which rescues the lethal sln1 defect by dephosphorylating accumulated Hog1p. Only transformants containing a functional histidine kinase that complements the loss of pRSPTP2 and sln1 can grow on 5-FOA medium under inducing conditions.

Biochemical Assay for Kinase Activity

FLAG-tagged ORFA protein was immunoprecipitated from *S. cerevisiae* JF2007 containing pESCTRP422 using an anti-FLAG antibody (Sigma, St. Louis, Mo.). C-myc tagged Sln1p was immunoprecipiated from *S. cerevisiae* JF2007 containing pGalSLN1 using an anti-myc antibody. (Sigma, St. Louis, Mo.). As a control, protein was immunoprecipitated from untransformed JF2007 using an anti-FLAG antibody.

A luminescent kinase assay (Promega, Madison, Wis.) was used to detect kinase activity in the protein extracts by measuring the residual amount of ATP in solution after a kinase reaction (M. Koresawa, T. Okabe, *Assay Drug Dev Technol* 2, 153 (2004)). The remaining ATP level directly correlates to the luminescence produced by luciferase added to the completed kinase reaction. Decreasing relative light units (RLU) indicates increasing kinase activity. The three protein extracts as well as the negative controls BSA and kinase reaction buffer were analyzed using this assay system.

Cell Wall Analysis

Lyophilized cells of *B. dermatitidis* were disrupted by bead-beating for analysis of chitin and other major components in the cell wall. Chitin was analyzed by the method described by Lehmann (P. F. Lehmann, L. O. White, *Infect Immun* 12, 987 (1975)). The amounts of α-1-3 glucan, β-1-3 glucan, and β-1-6 glucan in the cell wall were quantified by a modification of methods described by Dijkgraaf et al, and Boone et al (G. J. Dijkgraaf, J. L. Brown, H. Bussey, *Yeast* 12, 683 (1996); C. Boone, S. S. Sommer, A. Hensel, H. Bussey, *J Cell Biol* 110, 1833 (1990)).

To assay sensitivity to cell wall-binding chemicals, a strain was grown in liquid or solid media in the presence of either 20 μg/ml of calcofluor or Congo Red (Sigma) at 37° C. Mold was spotted inside a race tube (R. H. Davis, F. J. DeSerres, *Methods Enzymol* 17A, 79 (1970)) containing solid 3M medium with the addition of either 20 μg/ml of calcofluor or Congo Red and grown at 22° C.

Knockout of Histidine Kinase DRK1

*B. dermatitidis* isolates 60636 and 14081 were transformed with *A. tumefaciens* strain LBA1100 carrying the binary vector pJNKO2. pJNKO2 contains 1067 bases of DRK1 coding and 5' upstream sequence and 811 bases of DRK1 coding and 3' downstream sequence interrupted by hph for selection. Transformants were selected on 3M containing 100 μg/ml of hygromycin and 200 μM cefotaxime. Knockout colonies emerged as mold at 37° C., and appeared at a frequency of 0.5% of transformants in strain 60636 and 3.1% in strain 14081. Knockouts were complemented using the vector pJNA1, as described above.

RNAi in *B. dermatitidis* and *H. capsulatum*

*B. dermatitidis* isolates 60636 and 14081 were transformed with *A. tumefaciens* strain LBA1100 carrying either the binary vector pCTK4-422 or pCTS463-422. pCTK4-422 contains a 3.6 kb hairpin repeat of the *B. dermatitidis* DRK1 sequence and the nat1 marker. pCTS463-422 contains the same 3.6 kb hairpin repeat and the hph marker. As a control, *B. dermatitidis* was transformed with the binary vector lacking a target sequence. Transformants were selected on either nourseothricin or hygromycin-containing medium, as described above.

*H. capsulatum* 186ARura5 and a clinical isolate HcKD were also transformed with *A. tumefaciens* strain LBA1100 carrying either the binary vector pCTK4-422 or pCTS463 422 used above in *B. dermatitidis*. As a control, *H. capsulatum* was transformed with the binary vector lacking a target sequence. The DRK1 histidine kinase is 90% identical at the nucleotide level in *B. dermatitidis* and *H. capsulatum* strains 186AR (3439/3825 nucleotides) and G217B (3435/3825 nucleotides). Transformants were selected on nourseothricin or hygromycin-containing medium as described above. Transformants of 186ARura5 were selected and maintained on media with exogenous uracil added.

Experimental Pulmonary Infection of Mice to Assess Virulence

C57BL6 mice were infected with spores of the wild-type parent strain and three independent isogenic DRK1-silenced strains from each of the *B. dermatitidis* strains 14081 and 60636. Mice (n=10/group) received 104 or 106 spores intratracheally as previously described (P. J. Rooney, T. D. Sullivan, B. S. Klein, *Mol Microbiol* 39, 875 (2001)). Outcomes included survival over 70 days and burden of infection (CFU) in harvested lungs 14 days after infection. Data were analyzed statistically using the Wilcoxon Rank test (lung CFU) and Mantel-Haenszel test (survival) (M. Wuthrich, H. L Filutowicz, T. Warner, G. S. Deepe, Jr., B. S. Klein, *J Exp Med* 197, 1405 (2003)).

C57BL6 mice were also intratracheally infected with 108 spores of the wild-type strain HcKD and three independent isogenic DRK1-silenced strains of *H. capsulatum*. Outcomes included survival and burden of infection in harvested lungs at two time-points after infection. Data were analyzed as above.

Example II

Vaccination with DRK1-Silenced Yeast Protects Mice Against Lethal Pulmonary Infection Methods Fungi—Strains used were a patient isolate strain 14081 obtained from the State Lab of Hygiene and the isogenic DRK1-silenced strain, designated 14081 #2-6 (Nemecek, J. C., M. Wuthrich, and B. S. Klein. 2006. *Science* 312:583-588.). Isolates were maintained as yeast on Middlebrook 7H10 agar with oleic acid-albumin complex (Sigma Chemical Co., St. Louis, Mo.) at 37° C.

Vaccination and experimental infection—C57BL6 mice were vaccinated as described (Wüthrich, M., H. L. Filutowicz, and B. S. Klein. 2000. *J. Clin Invest* 106:1381-1389.) twice, two weeks apart, each time receiving a s.c. injection of 105 DRK1-silenced yeast at each of two sites, dorsally and at the base of the tail. After vaccination, mice were infected intratracheally with $2\times10^3$ wild-type yeast as described (Wüthrich, M, H. L. Filutowicz, and B. S. Klein. 2000. *J. Clin Invest* 106:1381-1389.), and sacrificed 19 days later to analyze extent of lung infection, which was determined by plating of homogenized lung and enumeration of yeast colony forming units (CFU) on Brain heart infusion (BHI) (Difco, Detroit, Mich.) agar.

Statistical Analysis—Differences in number of CFU were analyzed using the Wilcoxon Rank test for nonparametric data (Fisher, L. D., and G. van Belle. 1993. *Biostatistics: A Methodology for the Health Sciences*. John Wiley & Sons, New York.:611-613.). A P value of <0.05 is considered statistically significant.

Results

We reported that silencing expression of DRK1 reduces pathogenicity of *B. dermatitidis* in a murine model of pulmonary infection (Example I and Nemecek, J. C., M. Wuthrich, and B. S. Klein. 2006. *Science* 312:583-588). Referring to FIG. 11, we tested here whether the DRK1-silenced strain 14081 #2-6 vaccinates mice against infection after re-exposure to wild-type *B. dermatitidis*. After vaccination with the DRK1 silenced strain, mice were challenged with the virulent isogenic parent strain 14081. At 19 days post-infection, all vaccinated mice looked healthy whereas unvaccinated mice looked moribund. Lung CFU were reduced by five logs in vaccinated mice compared to unvaccinated controls (see FIG. 11). Thus, DRK1 silenced yeast used as a live attenuated vaccine protected mice against lethal experimental blastomycosis.

The invention claimed is

1. A dimorphic fungus, wherein the fungus has a reduced histidine kinase expression and wherein the fungus has a reduced ability to morph into the virulent yeast form, wherein the kinase has been inactivated via RNAi, and wherein the kinase is Dimorphism Regulating Kinase 1 (DRK-1).

2. An isolated dimorphic fungus, wherein the fungus has a reduced histidine kinase expression and a reduced ability to morph into the virulent yeast form, and wherein the histidine kinase is Dimorphism Regulating Kinase 1 (DRK-1).

3. An isolated dimorphic fungus, wherein the fungus has a reduced histidine kinase expression and a reduced ability to morph into the virulent yeast form, and wherein the histidine kinase is the Dimorphism Regulating Kinase 1 (DRK-1) homologue found in *C. immitis* or *H. capsulatum.*

* * * * *

SEQUENCE LISTING

<160> NUMBER OF SEQ ID NOS: 10

<210> SEQ ID NO 1
<211> LENGTH: 4004
<212> TYPE: DNA
<213> ORGANISM: Unknown
<220> FEATURE:
<223> OTHER INFORMATION: Blastomyces dermatitidis

<400> SEQUENCE: 1
satgactcgg ggtgatgaaa ccctgcttgc tgtagctggc atcctgcagg gtctggcaaa 60
ggatgtcccc gactccgcat cgctgccttt caacagctac aagtccaaca atgctaccaa 120
cggcgatgtg gcgaaaataa atctgccagg cgaaaacagc gatggtaagg cagttttgga 180
acgggagttg gaggatctga tccgtaggat cggtactatg caatgttttg tggttagttg 240
ccttcgaatc ctcctttata acactccttt caagagtcat tcttgtagag atcggatctc 300
tagggtggca ttacctctct ttgctgggaa aagaggtcta aaatttcatc atgctgacca 360

-continued

```
accttattta gcccccatcc cgacgatcta cccgcgcagc gatttccagt ggacaagaca    420
ctaattccca cgggtcacct aaacccctcc ccggatccga tgtgaactat gaagacgata    480
tacatttcct acagaaccga gttcaacttc aagcacaaga aatacaacta cagaaagatg    540
taatctccag ggttcgtgag gaactcaaag aacaggagaa aaataccgag aaagccctag    600
ggaaggtgaa aaaggaggat gtcggcatat tagagcggga actacgcaag caccaacagg    660
ccaacgaggc tttccaaaag gccttacgag aaattggcgg gatcatcaca caagttgcaa    720
atggagactt gtctatgaaa gttcagatcc atccgttaga aatggacccg gaaatcacga    780
catttaaacg cactattaat actatgatgg accaactcca ggttttcggg agcgaagtgt    840
caagagtggc ccgggaggtc ggaaccgaag gaatccttgg cgggcaagct cagattaccg    900
gagtccatgg tatctggaaa gagctgacgg aaaatgtaaa tatcatggcc aagaatctta    960
cagatcaagt ccgagaaatc gcaactgtca cgacagccgt cgcccatggt gatctcagcc   1020
agaagatcga aagcagagcc aaaggtgaaa ttttggagct tcagcaaacc atcaacacta   1080
tggtggatca acttcgtaca tttgctactg aagttacgcg ggtcgcccga gacgtgggca   1140
ctgagggtgt actaggtgga caagctcaga ttgagggagt ccaaggaatg tggaacgaac   1200
ttactgttaa tgtcaatgcc atggccgaaa atcttacgac ccaagtccgt gatattgcga   1260
tggtaacgac ggcggtcgcc aagggcgatc ttacacagaa agtccaggct aactgcaagg   1320
gtgaaattct tgctttgaaa acaattatca attccatggt tgaccaactg aagcaatttg   1380
cgcaagaggt cacaaaaatc gccaaggagg tcggaacaga tggtgtcctt ggtggccagg   1440
caactgttca tgatgtggaa ggaacttgga aggatctcac tgagaatgtt aacggcatgg   1500
ccatgaacct tactactcag gtccgcgaga ttgctgacgt taccactgct gtcgccaagg   1560
gtgacttgac aaagaaagtc actgcagacg tgaaaggcga aatattggat ttgaaaaaca   1620
caattaacgg aatggtggat agactgaaca ccttcgcctt cgaggtcagc aaagtggcgc   1680
gagaagtcgg cactgatggc actcttggcg gtcaggcaaa ggtggataac gtggagggta   1740
aatggaagga tttgaccgat aacgtcaaca ccatggctca aaatctgact tctcaggtga   1800
gagggatatc tgaagtaacc caagctattg ccaagggtga acttgcgaag aagatcgaag   1860
tccatgctca aggtgagata ctcactttga aagtgacgat caataacatg gtggaccgcc   1920
ttgccaactt cgcccacgag ctcaaacgag tggcgcgcga tgtcggagtc gacggaaaga   1980
tgggtggcca agccaacgtt gaaggaattg ctggtagatg gaaagagatc actgaggacg   2040
ttaacaccat ggctgaaaac ttgacatctc aagtgcgcgc tttcggagaa atcaccgatg   2100
cagccactga tggtgatttc accaaactaa tcaccgtgaa tgcttccggc gagatggacg   2160
agcttaagcg gaagatcaat aagatggttt cgaatcttcg agatagtatt cagcgaaaca   2220
ctgccgccag agaagcagca gaacttgcca accgcacaaa gtccgagttc ctcgcaaata   2280
tgagtcacga aatccgaacc ccgatgaacg gcatcatagg catgacacag ctgacgctag   2340
atactgacga cctcaagcca tacccgcgag agatgttgaa cgtggtgcat agcctagcca   2400
atagcttatt gacgattatt gacgatatcc tcgatatctc caagattgaa gcgaaccgca   2460
tggtcattga aaagattcca tttagcatga gaggcaccgt attcaacgcg cttaaaacct   2520
tagctgtaaa agccaacgag aagttcttga gccttgcgta ccaagtggat agttctgttc   2580
ccgactacgt cactggtgat ccgttcagat tacgtcaaat tatactaaac ttggtcggga   2640
acgcgatcaa atttacggaa catggggaag tcaaacttgc tatcagcaga tcggatcgag   2700
```

-continued

```
aggaatgtaa agataatgaa tacgcgttcg aattctccgt ttcggatact ggaatcggaa   2760

ttgaggaaga caagttggat ttgatcttcg ataccttcca gcaagctgac ggctcgacga   2820

ccaggaagtt cggaggaact ggtctggggc tatctatttc taagagatta gtgaatctca   2880

tgggtggtga tgtttgggtt acctctgaat atggcctcgg aagtagcttc cacttcacgt   2940

gcgttgtaga actggcagac cagtctatca gcatgattag cgcgtccctc atgccctaca   3000

aaaaccaccg tgttctgttc atcgacaaag gccagaccgg tggccacgca gaggaaatta   3060

ctgaaatgct gaagcagctt gacctagagc ccattgttgt gaaggatgaa tcgcaggtac   3120

caccaccgga aattcaggat cccacaggca aggattctgg acatgcttac gacgttataa   3180

tcgtcgactc cgtcgacacc gcgcgaaatc tgcgcacgta cgatgagttt aaatacatac   3240

ctatcgttct attatgccct gtcgtttctg tcagtctgaa gtcagcactg gatctgggta   3300

tcacatcgta catgacaact ccttgtcagc ctatcgatct aggcaatggc atgttgcctg   3360

ctcttgaagg acgttccacg ccaataacta cggaccacac aagatcgttt gatattcttt   3420

tggccgagga caacgatgtg aaccagaggg ttgccgtcaa gatactggag aaatgcaacc   3480

atggcgtgac cgttgtcagc aatggccttc aagctgtgga agcgatcaag aagcgtcgat   3540

acgacgtcat tttgatggat gtccaaatgc ctgttatggg aggattcgaa gctacgggca   3600

agatccgaga atatgaaaag aaaaacggac tatcacgaac gcccattatc gctttgaccg   3660

cacacgcgat gctcggtgac cgggagaaat gtatccaagc ccagatggat gaatacctgg   3720

ctaaacctct gaaacagaac cagatgattc aaaccatctt gaagtgcgca actctcggtg   3780

gttccctcct ggaaaagagc aaggagccaa gaatgtcgag cagcggcgag cctcctcacc   3840

acgtccccaa cagcaatgga atgaaatcac tagacacgaa gaaccaacga ccggggatgg   3900

acagtcaagc tacatcggca tctggtggtc ccaatccgaa tcagaaatct gacgtagtga   3960

gtacacgtca aacccgtgtg gctagttcgt ggactaaaga ttag                    4004


<210> SEQ ID NO 2
<211> LENGTH: 11
<212> TYPE: PRT
<213> ORGANISM: Saccharomyces cerevisiae
<220> FEATURE:
<221> NAME/KEY: DOMAIN
<222> LOCATION: (1)..(11)
<223> OTHER INFORMATION: H Box of histine kinase SLN1

<400> SEQUENCE: 2

Ser His Glu Leu Arg Thr Pro Leu Asn Gly Ile
1               5                   10


<210> SEQ ID NO 3
<211> LENGTH: 11
<212> TYPE: PRT
<213> ORGANISM: Unknown
<220> FEATURE:
<223> OTHER INFORMATION: Blstomyces dermatitidis, Cocidioides immitis
      and Histoplasma capsulatum
<220> FEATURE:
<221> NAME/KEY: DOMAIN
<222> LOCATION: (1)..(11)
<223> OTHER INFORMATION: H Box of histidine kinase in Blastomyces
      dermatitidis, Coccidioides immitis and Histoplasma capsulatum

<400> SEQUENCE: 3

Ser His Glu Ile Arg Thr Pro Met Asn Gly Ile
1               5                   10
```

-continued

<210> SEQ ID NO 4
<211> LENGTH: 10
<212> TYPE: PRT
<213> ORGANISM: Saccharomyces cerevisiae
<220> FEATURE:
<221> NAME/KEY: DOMAIN
<222> LOCATION: (1)..(10)
<223> OTHER INFORMATION: D Box in histindine kinase SLN1

<400> SEQUENCE: 4

Ile Glu Val Glu Asp Thr Gly Pro Gly Ile
1               5                   10

<210> SEQ ID NO 5
<211> LENGTH: 10
<212> TYPE: PRT
<213> ORGANISM: Unknown
<220> FEATURE:
<223> OTHER INFORMATION: Blstomyces dermatitidis, Cocidioides immitis
      and Histoplasma capsulatum
<220> FEATURE:
<221> NAME/KEY: DOMAIN
<222> LOCATION: (1)..(10)
<223> OTHER INFORMATION: D Box of histine kinse in Blastomyces
      dermatitidis, Coccidioides immitis and Histoplasma capsulatum

<400> SEQUENCE: 5

Phe Ser Val Ser Asp Thr Gly Ile Gly Ile
1               5                   10

<210> SEQ ID NO 6
<211> LENGTH: 16
<212> TYPE: PRT
<213> ORGANISM: Saccharomyces cerevisiae
<220> FEATURE:
<221> NAME/KEY: DOMAIN
<222> LOCATION: (1)..(16)
<223> OTHER INFORMATION: N Box of histine kinse SLN1

<400> SEQUENCE: 6

Ile Ile Gln Ile Val Met Asn Leu Val Ser Asn Ala Leu Lys Pro Thr
1               5                   10                  15

<210> SEQ ID NO 7
<211> LENGTH: 16
<212> TYPE: PRT
<213> ORGANISM: Unknown
<220> FEATURE:
<223> OTHER INFORMATION: Blstomyces dermatitidis, Cocidioides immitis
      and Histoplasma capsulatum
<220> FEATURE:
<221> NAME/KEY: DOMAIN
<222> LOCATION: (1)..(16)
<223> OTHER INFORMATION: N Box of histidine kinase in Blastomyces
      dermatitidis, Coccidioides immitis and Histoplasma capsulatum

<400> SEQUENCE: 7

Leu Arg Gln Ile Ile Leu Asn Leu Val Gly Asn Ala Ile Lys Phe Thr
1               5                   10                  15

<210> SEQ ID NO 8
<211> LENGTH: 37
<212> TYPE: PRT
<213> ORGANISM: Saccharomyces cerevisiae
<220> FEATURE:
<221> NAME/KEY: DOMAIN
<222> LOCATION: (1)..(37)
<223> OTHER INFORMATION: G Box of histidine kinase SLN1

<400> SEQUENCE: 8

-continued

```
Gly Thr Gly Leu Gly Leu Ser Ile Cys Arg Gln Leu Ala Asn Met Asn
1               5                   10                  15

His Gly Thr Met Lys Leu Glu Ser Lys Val Gly Val Gly Ser Lys Phe
            20                  25                  30

Thr Phe Leu Pro Leu
        35


<210> SEQ ID NO 9
<211> LENGTH: 37
<212> TYPE: PRT
<213> ORGANISM: Unknown
<220> FEATURE:
<223> OTHER INFORMATION: Blstomyces dermatitidis and Histoplasma
      capsulatum

<400> SEQUENCE: 9

Gly Thr Gly Leu Gly Leu Ser Ile Ser Lys Arg Leu Val Asn Leu Met
1               5                   10                  15

Gly Gly Asp Val Trp Val Thr Ser Glu Tyr Gly Leu Gly Ser Ser Phe
            20                  25                  30

His Phe Thr Cys Val
        35


<210> SEQ ID NO 10
<211> LENGTH: 37
<212> TYPE: PRT
<213> ORGANISM: Coccidioides immitis
<220> FEATURE:
<221> NAME/KEY: DOMAIN
<222> LOCATION: (1)..(37)
<223> OTHER INFORMATION: G Box of histidine kinase in Coccidioides
      immitis

<400> SEQUENCE: 10

Gly Thr Gly Leu Gly Leu Ser Ile Ser Lys Arg Leu Val Asn Leu Met
1               5                   10                  15

Gly Gly Asp Val Trp Val Ser Thr Glu Phe Gly His Gly Ser Thr Phe
            20                  25                  30

His Phe Thr Cys Lys
        35
```